(12) United States Patent
Gullapalli et al.

(10) Patent No.: US 8,501,785 B2
(45) Date of Patent: Aug. 6, 2013

(54) SALTS OF BENZIMIDAZOLYL PYRIDYL ETHERS AND FORMULATIONS THEREOF

(75) Inventors: Rampurna Gullapalli, San Bruno, CA (US); Ahmad Hashash, Pleasant Hill, CA (US); Piotr Karpinski, Lincoln Park, NJ (US); Kangwen L. Lin, Fremont, CA (US); Eric M. Loeser, Scotch Plains, NJ (US); Augustus O. Okhamafe, Concord, CA (US); Paul Allen Sutton, Parsippany, NJ (US); Eduardo Sy, Union City, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/488,241

(22) Filed: Jun. 4, 2012

(65) Prior Publication Data

US 2012/0308651 A1 Dec. 6, 2012

Related U.S. Application Data

(62) Division of application No. 12/377,901, filed as application No. PCT/US2007/019152 on Aug. 30, 2007, now Pat. No. 8,202,998.

(60) Provisional application No. 60/954,466, filed on Aug. 7, 2007, provisional application No. 60/841,177, filed on Aug. 30, 2006.

(51) Int. Cl.
  *A61K 31/4439* (2006.01)
  *A61K 9/48* (2006.01)

(52) U.S. Cl.
  USPC .......................................... 514/338; 424/451

(58) Field of Classification Search
  USPC .......................................... 514/338; 424/451
  See application file for complete search history.

(56) References Cited

U.S. PATENT DOCUMENTS

| 7,482,367 B2 * | 1/2009 | Aikawa et al. ................. 514/338 |
| 7,732,465 B2 * | 6/2010 | Aikawa et al. ................. 514/338 |
| 8,202,998 B2 * | 6/2012 | Gullapalli et al. ......... 546/273.4 |
| 2006/0189619 A1 | 8/2006 | Tadayon et al. |
| 2007/0049622 A1 | 3/2007 | Dimitroff et al. |
| 2010/0040677 A1 | 2/2010 | Hashash et al. |
| 2010/0168060 A1 | 7/2010 | Gullapalli et al. |
| 2010/0189619 A1 | 7/2010 | Kolis et al. |

FOREIGN PATENT DOCUMENTS

| WO | WO 03/082272 | 10/2003 |
| WO | WO 2005/032548 | 4/2005 |
| WO | WO 2007/030377 | 3/2007 |
| WO | WO 2008/011154 | 1/2008 |

OTHER PUBLICATIONS

Amiri et al., Proceedings of the American Association for Cancer Research Annual Meeting, 2006, vol. 47, Abstract #4855.
Boyer, Raf modulators and methods of use. Expert Opin Ther Pat. 2006 Jul; 16(7):1031-6.
Bataille V., Clinical and Experimental Dermatology, 2006, vol. 31, No. 4, p. 617-619.
Burley, Stephen K., Genome Biology, 2006, vol. 7, No. 4, Article 314.
Hashida, M. Design and Evaluation of Oral Drug, Jiho Inc., 1995, p. 76-79. (Japanese) and English translation of Office Action issued in the corresponding JP application JP2009-526734 citing the reference.
Venetsanakos et al., Proceedings of the American Association for Cancer Research Annual Meeting, 2006, vol. 47, Abstract #4854.

\* cited by examiner

*Primary Examiner* — Jennifer M Kim
(74) *Attorney, Agent, or Firm* — Foley & Lardner LLP

(57) ABSTRACT

Salts of benzimidazolyl pyridyl ethers are provided, particularly salts of {1-methyl-5-[2-(5-trifluoromethyl-1H-imidazol-2-yl)-pyridin-4-yloxy]-1H-benzoimidazol-2-yl}-(4-trifluoromethyl-phenyl)amine. Compositions and formulations including such salts and surfactants as well as methods of preparing such compositions and formulations are provided.

24 Claims, 14 Drawing Sheets

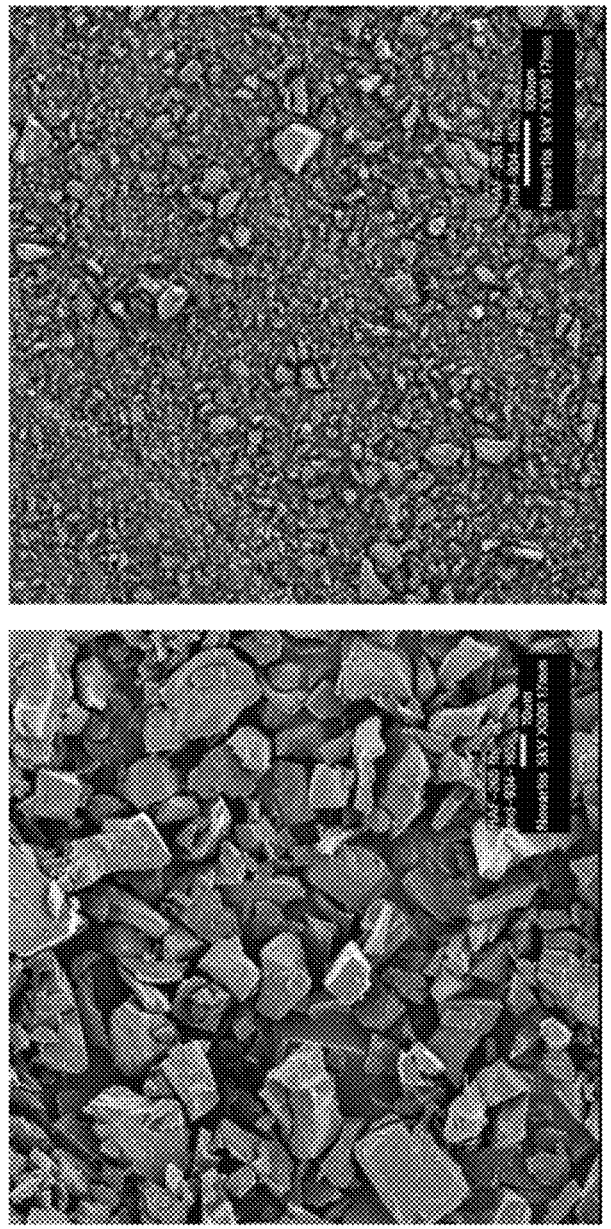
FIG. 1A. API Free Base

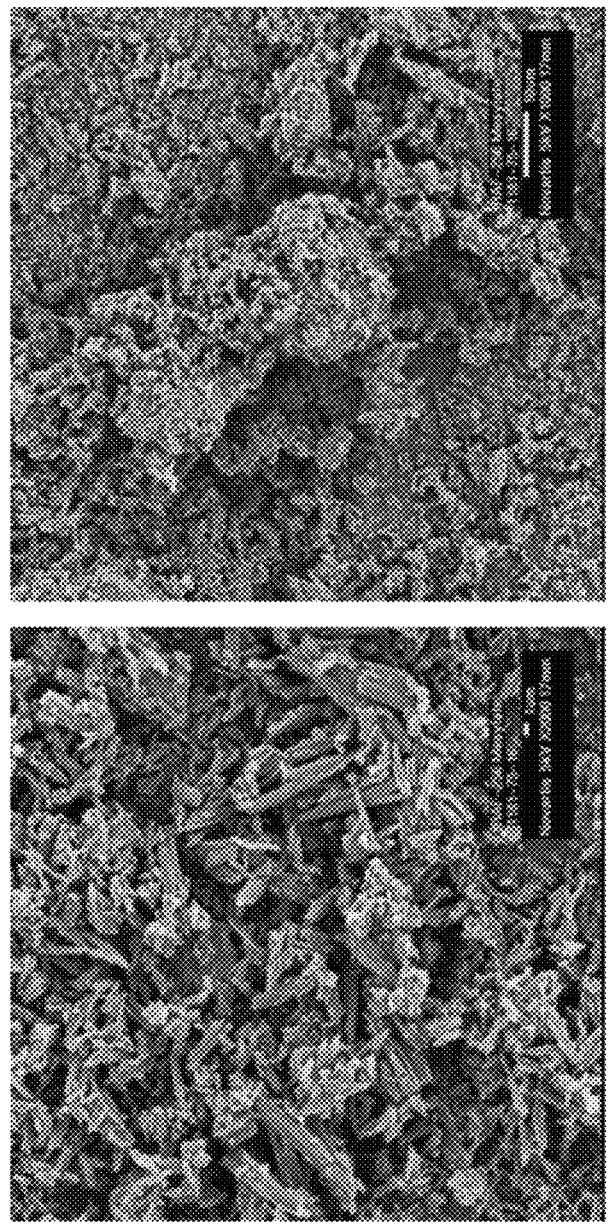
FIG. 1B. API Mesylate Salt

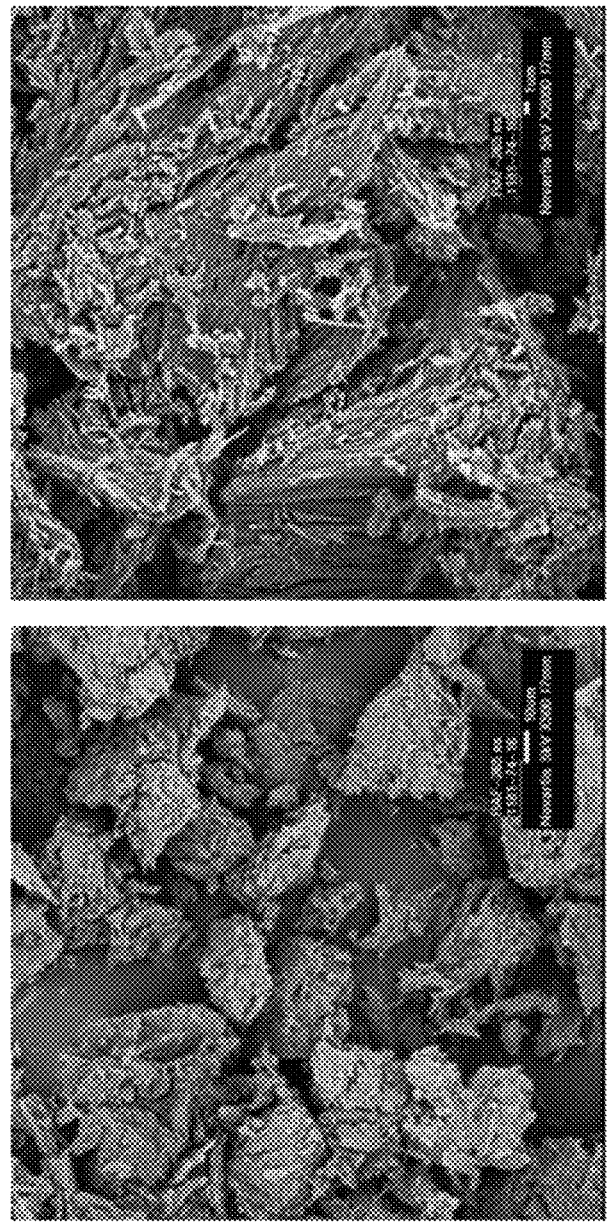
FIG. 1C. API Esylate Salt

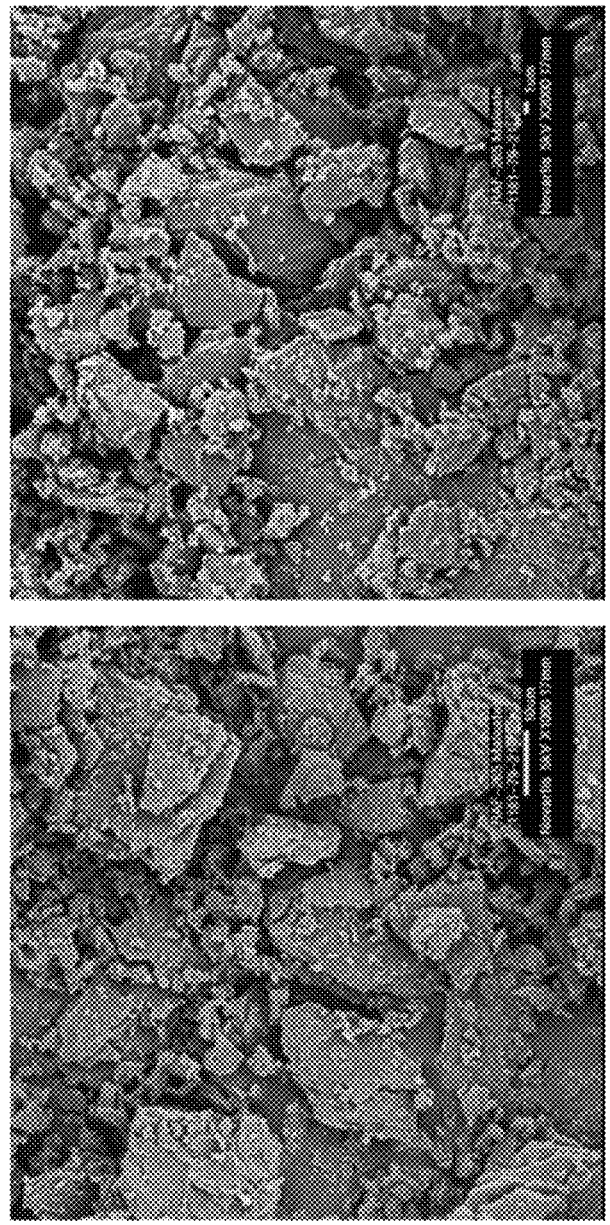
FIG. 1D. API Maleate Salt

SALTS OF BENZIMIDAZOLYL PYRIDYL ETHERS AND FORMULATIONS THEREOF

CROSS-REFERENCE TO RELATED APPLICATIONS

This application is a divisional of U.S. application Ser. No. 12/377,901, filed 13 Apr. 2009, now U.S. Pat. No. 8,202,998, which is a National Stage of International Application No. PCT/US2007/019152, filed 30 Aug. 2007, which claims benefit of U.S. Provisional Application No. 60/841,177, filed 30 Aug. 2006, and U.S. Provisional Application No. 60/954,466, filed 7 Aug. 2007, all of which in their entirety are herein incorporated by reference.

FIELD OF THE INVENTION

This invention pertains generally to salts of benzimidazolyl pyridyl ether compounds and formulations of such salts. More specifically, the disclosure herein pertains to salts and dosage formulations comprising salts of {1-methyl-5-[2-(5-trifluoromethyl-1H-imidazol-2-yl)-pyridin-4-yloxy]-1H-benzoimidazol-2-yl}-(4-trifluoromethyl-phenyl)amine, and mixtures thereof, and to methods for preparing and using such formulations.

BACKGROUND

The involvement of kinases in the development of cancer is well known. For example, kinases known to be associated with tumorigenesis include the Raf serine/threonine kinases and the receptor tyrosine kinases (RTKs). Both types of kinases are part of a signal transduction pathway which ultimately phosphorylates transcription factors. Within the pathway, Raf kinases are part of the Ras/Mitogen-Activated Protein Kinase (MAPK) signaling module that influence and regulate many cellular functions such as proliferation, differentiation, survival, oncogenic transformation and apoptosis.

Several Raf kinase inhibitors have been described as exhibiting efficacy in inhibiting tumor cell proliferation in vitro and/or in vivo assays (see, e.g., U.S. Pat. Nos. 6,391,636, 6,358,932, 6,037,136, 5,717,100, 6,458,813, 6,204,467, and 6,268,391). Other patents and patent applications suggest the use of Raf kinase inhibitors for treating leukemia (see, e.g., U.S. Pat. Nos. 6,268,391, and 6,204,467, and published U.S. Patent Application Nos. 20020137774; 20020082192; 20010016194; and 20010006975), or for treating breast cancer (see, e.g., U.S. Pat. Nos. 6,358,932; 5,717,100; 6,458,813; 6,268,391; and 6,204,467, and published U.S. Patent Application No. 20010014679). In early clinical trials, inhibitors of Raf-1 kinase that also inhibit B-Raf have shown promise as therapeutic agents in cancer therapy (Crump, *Current Pharmaceutical Design* 8:2243-2248 (2002); Sebastien et al., *Current Pharmaceutical Design* 8: 2249-2253 (2002)).

Receptor tyrosine kinases (RTKs), such as vascular endothelial growth factor receptors (VEGFR), are transmembrane polypeptides that regulate developmental cell growth and differentiation, remodeling, and regeneration of adult tissues. Mustonen, T. et al., *J. Cell Biology* 129:895-898 (1995); van der Geer, P. et al., *Ann Rev. Cell Biol.* 10:251-337 (1994). VEGF and members of the VEGF subfamily are able to induce vascular permeability and endothelial cell migration and proliferation, as welt as induce angiogenesis and vasculogenesis, Ferrara, N. et al., *Endocrinol. Rev.* 18:4-25 (1997); Connolly, D. et al., *J. Biol. Chem.* 264:20017-20024 (1989); Connolly, D. et al., *J. Clin. Invest.* 84:1470-1478 (1989); Leung, D. et al., *Science* 246:1306-1309 (1989); Plouet, J. et al., *EMBO J* 8:3801-3806 (1989).

Angiogenesis is the process whereby new blood vessels are formed in a tissue, and is critical to the growth of cancer cells. In cancer, once a nest of cancer cells reaches a certain size, roughly 1 to 2 mm in diameter, the cancer cells must develop a blood supply in order for the tumor to grow larger as diffusion is not sufficient to supply the cancer cells with enough oxygen and nutrients. Thus, inhibition of angiogenesis by the inhibition of kinases involved in angiogenesis is expected to halt the growth of cancer cells.

One class of compounds that inhibit angiogenesis, inhibit the growth of tumors, treat cancer, modulate cell cycle arrest, and/or inhibit kinases such as Ras, Raf mutant B-Raf, VEGFR2 (KDR, Flk-1), FGFR2/3, c-Kit, PDGFRβ, CSF-1R is the class of compounds known as benzimidazolyl pyridyl ethers. Methods for the synthesis and use of various benzimidazolyl pyridyl ether compounds have been disclosed in WO 2003/082272 and WO 2005/032458, in U.S. Provisional Application Nos. 60/712,539 filed on Aug. 30, 2005; 60/731, 591 filed on Oct. 27, 2005; 60/774,684 filed on Feb. 17, 2006; 60/713,108 filed on Aug. 30, 2005, and 60/832,715, filed Jul. 21, 2006, and in the U.S. utility application entitled "Substituted Benzimidazoles And Methods Of Their Use," filed Aug. 30, 2006 (U.S. Ser. No. 11/513,959), and the U.S. utility application entitled "Substituted Benzimidazoles And Methods Of Preparation," filed Aug. 30, 2006 (U.S. Ser. No. 11/513,745), the entire disclosures of which are herein incorporated by reference for all purposes. Despite the excellent biological activity shown by benzimidazolyl pyridyl ethers, challenges in formulating this class of compounds exist due to the low water solubility of the compounds at physiological pH.

SUMMARY

In one aspect, the invention provides salts of benzimidazolyl pyridyl ethers and methods of making such salts. In some embodiments, salts of the invention are selected to have substantially improved aqueous solubility over the free base, e.g., 2 times or more. In another aspect the invention provides compositions, formulations and medicaments of salts of benzimidazolyl pyridyl ethers and methods of making and using such compositions, formulations and medicaments. The formulations include solid and liquid formulations of salts of {1-methyl-5-[2-(5-trifluoromethyl-1H-imidazol-2-yl)-pyridin-4-yloxy]-1H-benzoimidazol-2-yl}-(4-trifluoromethyl-phenyl)amine in capsule and tablet form, as well as in parenteral forms, among others. The formulations may be administered orally or by other methods known in the art. Formulations of the invention provide improved aqueous solubility, faster dissolution rates and improved in vivo exposure/pharmacokinetics of the benzimidazolyl pyridyl ether compounds compared to the unformulated compounds, such as the free base and salts thereof.

In one aspect, the present invention provides salts of benzimidazolyl pyridyl ethers such as {1-methyl-5-[2-(5-trifluoromethyl-1H-imidazol-2-yl)-pyridin-4-yloxy]-1H-benzoimidazol-2-yl}-(4-trifluoromethyl-phenyl)amine. The latter compound has the structure of Formula I:

I

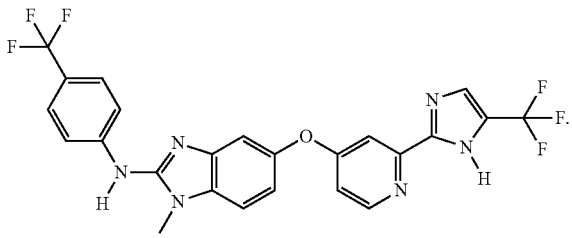

Salts of the compound of Formula I include acetate, tosylate, succinate, lactate, malate, sulfate, maleate, citrate, hydrochloride, phosphate, ethanesulfonate, and methanesulfonate salts. In some embodiments, the salts are selected to have a minimum solubility in aqueous solution of at least 0.058 mg/mL.

In another aspect, the invention provides compositions comprising a pharmaceutically acceptable acid salt of benzimidazolyl pyridyl ethers such as {1-methyl-5-[2-(5-trifluoromethyl-1H-imidazol-2-yl)-pyridin-4-yloxy]-1H-benzoimidazol-2-yl}-(4-trifluoromethyl-phenyl)amine and a surfactant. While many pharmaceutically acceptable acids may be used as the cognate acid in acid salts of the invention, the cognate acid of the acid salt typically has a pKa of about 4.7 or less than 4.7. For example, the cognate acid of the acid salt can be acetic acid, toluene sulfonic acid, succinic acid, lactic acid, malic acid, sulfuric acid, maleic acid, citric acid, hydrochloric acid, phosphoric acid, ethanesulfonic acid, and methanesulfonic acid.

Any suitable surfactant may be used in compositions and methods of the invention, including for example, surfactants having an HLB value of about 8 or higher than 8. Exemplary surfactants include polyoxyethylene castor oil compounds, polyoxyethylene mono- and di-fatty acid esters, mixtures of polyoxyethylene mono- and di-esters of $C_8$-$C_{22}$ fatty acids and glyceryl mono-, di-, and tri-esters of $C_8$-$C_{22}$ fatty acids, d-α-tocopheryl polyethylene glycol 1000 succinate, polyoxyethylene-polyoxypropylene copolymers, polyoxyethylene sorbitan fatty acid esters, polyoxyethylene alkyl ethers, sodium dioctyl sulfosuccinate, sodium lauryl sulfate, sorbitan fatty acid esters, sugar fatty acid esters, or a mixture of any two or more thereof.

In another aspect, formulations described herein may be contained within a capsule or tablet. In some embodiments, the total mass of the compound of Formula I, a pharmaceutically acceptable salt thereof, or a mixture of any two or more thereof, contained within the capsule or tablet, ranges from about 0.01 mg to about 400 mg. In some embodiments, the capsule or tablet is coated with a polymer or gelatin, or is encapsulated within a gelatin sheath. The capsule may be a hard shell capsule ad may further have a band-sealed head section and a body section.

In another aspect, methods are provided for producing formulations of the invention. The methods may include combining a pharmaceutically acceptable acid salt of {1-methyl-5-[2-(5-trifluoromethyl-1H-imidazol-2-yl)-pyridin-4-yloxy]-1H-benzoimidazol-2-yl}-(4-trifluoromethyl-phenyl) amine and a surfactant to provide a composition/formulation as described herein. Alternatively, the methods include combining a compound, {1-methyl-5-[2-(5-trifluoromethyl-1H-imidazol-2-yl)-pyridin-4-yloxy]-1H-benzoimidazol-2-yl}-(4-trifluoromethyl-phenyl)amine, a pharmaceutically acceptable acid, and a surfactant to provide compositions as described herein. In some embodiments, the compound of Formula I, acid, and surfactant are combined by mixing the compound and acid together to provide a salt of the compound, and subsequently mixing the salt of the compound with the surfactant to provide a composition as described herein. The compound of Formula I and the acid can be mixed alone to form a paste or by dissolving the compound and the acid in an organic solvent to form the salt of the compound in situ.

There are also provided in some embodiments, a pharmaceutical packaging container, comprising: a storage vessel comprising one or more capsules or tablets, the one or more capsules or tablets comprising a formulation as embodied herein.

Salts of the compound of Formula I and formulations thereof are useful in/as pharmaceutical formulations or medicaments in the treatment of cancer and/or inhibition of angiogenesis in a subject in need thereof. Thus, in another aspect, there are provided methods for treating cancer and/or inhibiting angiogenesis in a subject, comprising administering the salts or formulations to the subject. Any of the salts described herein may be used, including but not limited to the mesylate, esylate and maleate salts. In some embodiments related to methods of treating cancer, the salt or formulation is administered in an amount sufficient to provide a $C_{max}$ after a single dose administration of from about 0.1 to about 6,000 ng/mL, about 0.1 to 1,000 ng/mL, about 0.1 to 500 ng/mL, about 1 to 150 ng/mL, or 1 to 10 ng/mL of the compound of Formula I, a pharmaceutically acceptable salt thereof, or a mixture of any two or more thereof, in the subject's plasma.

In other embodiments related to methods of treating cancer, the salt or formulation is administered in an amount sufficient to provide a $C_{max}$ at steady-state after administration of once, twice, three, four times or more daily or weekly of about 0.1 to about 6,000 ng/mL, about 0.1 to 1,000 ng/mL, about 0.1 to 500 ng/mL, about 1 to 150 ng/mL or 1 to 10 ng/mL of the compound of Formula I, a pharmaceutically acceptable salt thereof, or a mixture of any two or more thereof, in the subject's plasma.

In other embodiments related to methods of treating cancer, the salt or formulation is administered in an amount sufficient to maintain a $C_{min}$ at steady-state after administration of once, twice, three, four times or more daily or weekly of about 0.1 to about 6,000 ng/mL, about 0.1 to 1,000 ng/mL, about 0.1 to 500 ng/mL, about 1 to 150 ng/mL or 1 to 10 ng/mL of the compound of Formula I, a pharmaceutically acceptable salt thereof, or a mixture of any two or more thereof, in the subject's plasma.

In other embodiments of the method for treating cancer, the formulation is administered in an amount sufficient to provide an AUC from time-zero to time-infinity after a single oral dose administration of about 0.01 to about 2,500 μg*h/mL, about 1 to about 2,500 μg*h/mL, about 1 to about 2,000 μg*h/mL, about 1 to about 1,000 μg*min/mL, about 1 to about 100 μg*h/mL or about 1 to 10 μg*h/mL of the compound of Formula I, a pharmaceutically acceptable salt thereof, or a mixture of any two or more thereof, in the subject's plasma.

In other embodiments of the method for treating cancer, the formulation is administered in an amount sufficient to provide an AUC during a dosing interval at steady-state after administration of once, twice, three, four times daily or weekly of about 0.01 to about 2,500 μg*h/mL, about 1 to about 2,5000 μg*h/mL, about 1 to about 2,000 μg*h/mL, about 1 to about 1,000 μg*h/mL, about to about 100 μg*h/mL, about 0.1 to 10 μg*h/mL or about 0.1 to 1 μg*h/mL of the compound of Formula I, a pharmaceutically acceptable salt thereof, or a mixture of any two or more thereof, in the subject's plasma. In such treatment methods, the formulation is administered once, twice, three, four times, or more daily or weekly.

In other embodiments related to methods of treating cancer, the salt or formulation is administered in an amount sufficient to maintain $C_{min}$ of the compound of Formula I, a pharmaceutically acceptable salt thereof, or a mixture of any two or more thereof, in subject's plasma during a dosing interval at steady-state of about 0.1 to about 6,000 ng/mL, about 0.1 to 1,000 ng/mL, about 0.1 to 500 ng/mL, about 1 to 150 ng/mL or 1 to 10 ng/mL. To allow rapid achievement of steady-state plasma concentration level, a loading dose of the salt or formulation may be administered prior to the daily administration of the salt or formulation. The ratio of the amount of loading dose to amount of the daily dose is about 3 to 20.

In other embodiments of the method for treating cancer, the cancers to be treated include, but are not limited to, bladder, breast, brain, head and neck, liver, biliary tract, carcinomas, acute and chronic lymphoid leukemias, acute and chronic myelogenous leukemia, chronic myelomonocytic leukemias, colorectal, gastric, gastrointestinal stromal, glioma, lymphomas, melanomas, multiple myeloma, myelo-proliferative diseases, neuroendocrine, lung, small cell lung, pancreatic, prostate, renal cell, sarcomas and thyroid cancers.

BRIEF DESCRIPTION OF THE FIGURES

FIG. 1A: SEM Micrograph of compound of Formula I as free base.
FIG. 1B: SEM Micrograph of compound of Formula I as mesylate salt.
FIG. 1C: SEM Micrograph of compound of Formula I as esylate salt.
FIG. 1D: SEM Micrograph of compound of Formula I as maleate salt.

DETAILED DESCRIPTION

Figure 2A:
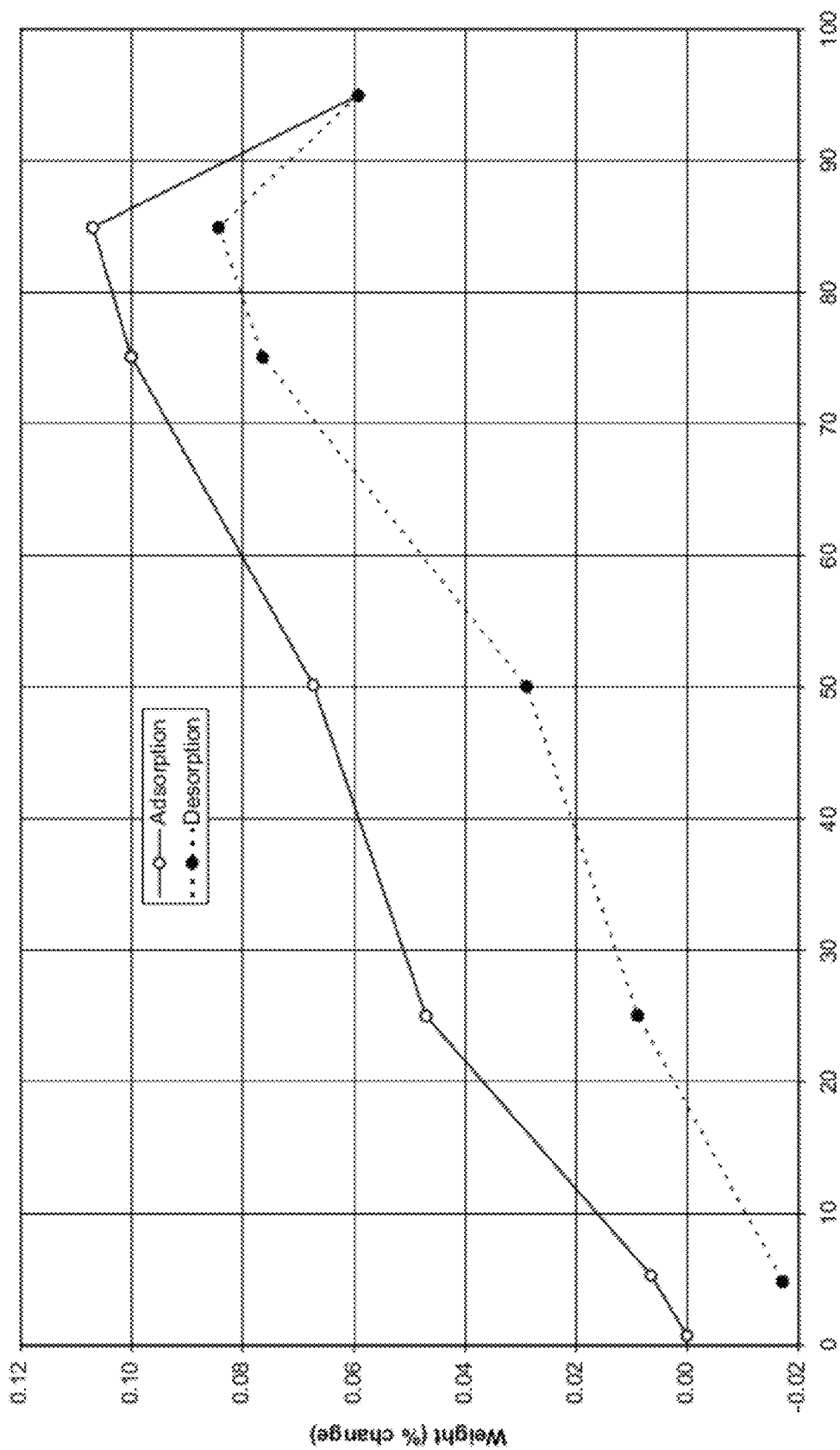
FIG. 2A: Sorption results for compound of Formula I as free base.
Figure 2B:
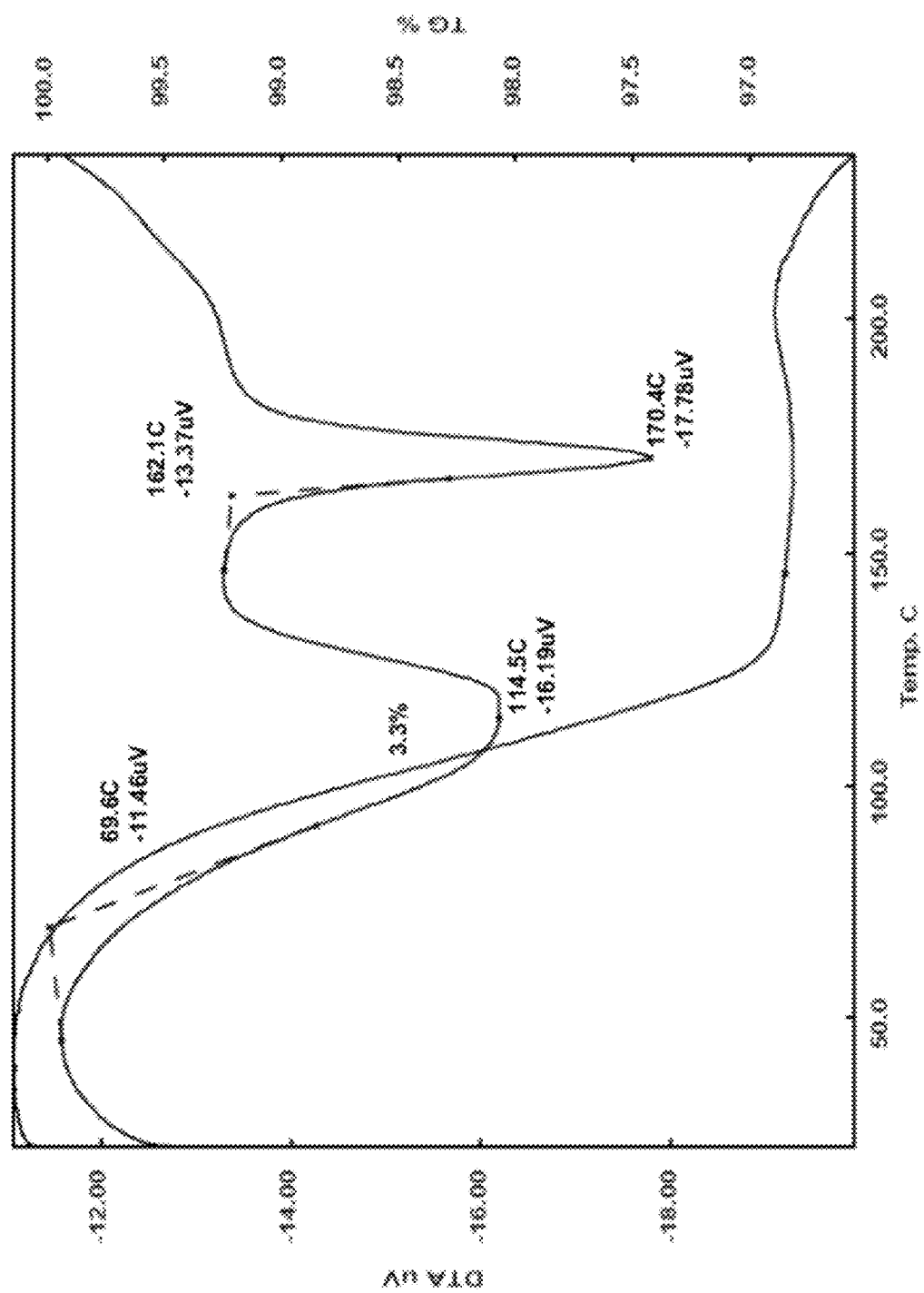
FIG. 2B: TG/DTA results for compound of Formula I as free base.

Salts and formulations of salts of benzimidazolyl pyridyl ether compounds are provided. Such formulations may be used to inhibit RAF kinase, an important kinase enzyme in the MAPK pathway. The formulations are useful, for example, in treating patients with cancer and/or a need for an inhibitor of RAF kinase.

The following abbreviations and definitions are used throughout this application:

"Adsorbent carrier" refers to materials, usually solid, employed to adsorb and/or absorb a liquid formulation.

"API" is an abbreviation thr active pharmaceutical ingredient. As used herein, unless otherwise noted, API refers to the compound: {1-methyl-5-[2-(5-trifluoromethyl-1H-imidazol-2-yl)-pyridin-4-yloxy]-1H-benzoimidazol-2-yl}-(4-trifluoromethyl-phenyl)amine.

"AUC" is an abbreviation for area under the curve in a graph of the concentration of a compound in blood plasma over time.

"Cellulose" includes the various forms of cellulose known for use in pharmaceutical formulations, including but not limited to, ethyl cellulose, cellulose acetate, carboxymethyl cellulose calcium, sodium carboxymethyl cellulose, methyl cellulose, hydroxyethyl cellulose, hydroxypropyl cellulose, hydroxypropyl methyl cellulose, (e.g., Nos. 2208, 2906, 2910), hydroxypropylmethyl cellulose phthalate, microcrystalline cellulose, and mixtures thereof. Suitable forms of microcrystalline cellulose for use in formulations of the invention include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof.

"$C_{max}$" is an abbreviation that refers to the maximum observed concentration of a compound in the plasma, tissue, or blood of a subject to which the compound has been administered. $C_{max}$ typically occurs within several minutes to several hours following administration of a compound to a subject, and is dependent upon the intrinsic physicochemical and biological properties of the compound.

"$C_{min}$" is an abbreviation that refers to the minimum observed concentration of a compound in the plasma, tissue, or blood of a subject during a time interval between administrations of the compound. $C_{min}$ typically occurs at the end of the interval between times of compound administration.

"Steady-state", as used herein, refers to the time during repeated administration of a compound at a fixed dosing schedule when $C_{max}$ and $C_{min}$ in each dosing interval become constant over time. $C_{max}$ and $C_{min}$ in each dosing interval may increase at the beginning of the repeated administration of a compound at a fixed dosing schedule. Eventually after some time period the $C_{max}$ and $C_{min}$ in a dosing interval will no longer increase and remain constant over time and are considered at steady-state. Time to reach "steady-state" after repeated administration of a compound at a fixed dosing schedule depends on the rate of elimination of the compound in subject's blood.

Croscarmellose sodium is cross-linked sodium carboxymethyl cellulose.

"Crospovidone" is a water-insoluble cross-linked homopolymer of 1-vinyl-2-pyrrolidinone typically having an empirically determined average molecular weight of greater than 1,000,000.

"Cyclodextrin" refers to a family of cyclic oligosaccharides containing at least six D-(+)-glucopyranose units.

"DMSO" is an abbreviation for dimethylsulfoxide.

"EtOAc" is an abbreviation for ethyl acetate.

"EtOH" is an abbreviation for ethanol.

"Fatty acid," as used herein, refers to any of the members of a large group of monobasic acids, especially those found in animal and vegetable fats and oils. In some embodiments the fatty acid is straight or branched chain alkyl or alkenyl group having 6 to 22 carbons, wherein the carboxylic acid is at one terminus of the carbon chain.

"Glycerides," as used herein, refers to esters formed between one or more acids and glycerol. In some embodiments, the acids are fatty acids. Medium-chain glycerides are glycerol esters of medium-chain fatty acids containing from 6 to 12 carbon atoms, or, in some embodiments, 6 to 10 carbon atoms. Medium chain fatty acids include: caproic acid (C6); caprylic acid (C8), capric acid (C10), and lauric acid (C12). Long chain glycerides are glycerol esters of long chain fatty acids containing from 12 to 22 carbon atoms, or in some embodiments, 12 to 18 carbon atoms.

"HDPE" is an abbreviation for high density polyethylene.

"HGC" is an abbreviation for hard gelatin capsule.

"HLB" is an abbreviation for hydrophilic-lipophilic balance. It is the ratio of water-soluble to oil-soluble portions of a molecule and is calculated according to the following formula:

HLB=% hydrophile by weight of molecule/5.

(Griffin W C, Classification of Surface-Active Agents by 'HLB'; *Journal of the Society of Cosmetic Chemists* 1 (1949) 311; Griffin W C, Calculation of HLB Values of Non-Ionic Surfactants; *Journal of the Society of Cosmetic Chemists* 5 (1954) 259.)

"HPLC" is an abbreviation for high performance liquid chromatography.

"HPMC" is an abbreviation for hydroxypropyl methylcellulose.

"Hr" is an abbreviation for hour(s).

"Hydrophilic," as used herein, refers to a material that readily dissolves in water or dissolves water. "Hydrophilic solvents" are solvents, which dissolve or disperse a solute and which itself also dissolve in water or dissolve water.

"LAH" is an abbreviation for lithium aluminum hydride.

"Lipid," as used herein, refers to any of a group of organic compounds, including, but not limited to the fats, oils, waxes, sterols, and triglycerides, that are insoluble in water but soluble in nonpolar organic solvents, and are oily to the touch.

"Lipophilic," as used herein, refers to a material that readily dissolves in lipids or dissolves lipids. "Lipophilic solvents" are solvents which dissolve or disperse a solute and which itself dissolves in lipids or dissolves lipids.

"LCMS" is an abbreviation for liquid chromatography mass spectroscopy.

"MeOH" is an abbreviation for methanol.

"MPEG" is an abbreviation for methoxypolyethylene glycol, a polyether having the general formula $CH_3O[CH_2CH_2O]_nH$, and having a wide range of average molecular weight. As used herein and except as otherwise indicated, MPEG may have an average molecular weight of front about 100 to about 20,000 g/mol, or higher.

"MTBE" is an abbreviation for methyl-tert-butyl ether.

"NMR" is an abbreviation for nuclear magnetic resonance.

"PEG" is an abbreviation for polyethyleneglycol, a polyether polymer of ethylene glycol having the general formula $HO[CH_2CH_2O]_nH$, and having a wide range of average molecular weight. In some embodiments of the present invention, the PEG has an average molecular weight of from about 1,000 g/mol to about 20,000 g/mol. In other embodiments, the PEG has an average molecular weight of from about 1,000 g/mol to about 10,000 g/mol, and in other embodiments, from about 1,000 to about 4,000 g/mol.

"Phospholipid," as used herein, refers to phosphorous-containing lipids that are composed mainly of fatty acids, a phosphate group, and a simple organic molecule, e.g. glycerol. Phospholipids may also be referred to as phosphatides.

"PEO" is an abbreviation for polyethylene oxide. As used herein, and except as otherwise indicated, polyethylene oxide is a polyether polymer of ethylene glycol having an average molecular weight of greater than 20,000 g/mol. In some embodiments, the average molecular weight of PEO is from greater than 20,000 up to 300,000 g/mol. PEO may be used in the form of copolymers with other polymers.

The apparent pKa of the compound of Formula I refers to the apparent ionization constant of the compound of Formula I as determined by a pH profile solubility study. Thus, the apparent pKa of the compound of Formula I is a complex term consisting of three overlapping ionization constants of the basic nitrogens in Formula I.

Povidone, as used herein, is a polymer of 1-vinyl-2-pyrrolidinone, and having a wide range of average molecular weight. In some embodiments, the povidone has an average molecular weight of from about 2,500 g/mol to about 300,000 g/mol, or greater.

"RH" is an abbreviation for relative humidity.

"rt" is an abbreviation for room temperature.

"SEDDS" is an abbreviation for self-emulsifying drug delivery systems.

Simulated gastric fluid, as used herein, refers to simulated gastric fluid USP/NF.

"SMEDDS" is an abbreviation for self-microemulsifying drug delivery systems.

"Sorbitan," as used herein, refers to dehydrated Sorbitol.

"Starch" refers to a complex carbohydrate consisting of amylase and amylopectin. "Pregelatinized starch" is starch that has been chemically and/or mechanically processed to rupture all or part of the granules in the presence of water and subsequently dried. Some types of pregelatinized starch may be modified to render them compressible and flowable in character.

"Sugar fatty acid," as used herein, refers to a fatty acid with a sugar moiety attached.

"Surfactant," as used herein, stands for "surface active agent", and is a substance which lowers the surface tension of the medium in which it is dissolved, and/or lowers the interfacial tension with other phases, and, accordingly, is positively adsorbed at the liquid/vapor and/or at other interfaces. The term surfactant further includes sparingly soluble substances which lower the surface tension of a liquid by spreading spontaneously over the surface of the liquid.

"TBACl" is an abbreviation for tert-butylammonium chloride.

"TFAA" is an abbreviation for trifluoroacetic anhydride.

"THF" is an abbreviation for tetrahydrofuran.

"TLC" is an abbreviation for thin layer chromatography.

A "pharmaceutically acceptable salt" includes a salt with an inorganic base, organic base, inorganic acid, organic acid, or basic or acidic amino acid. Salts of inorganic bases include, e.g., alkali metals such as sodium or potassium; alkaline earth metals such as calcium and magnesium or aluminum; and ammonia. Salts of organic bases include, e.g., trimethylamine, triethylamine, pyridine, picoline, ethanolamine, diethanolamine, and triethanolamine. Salts of inorganic acids include, e.g., hydrochloric acid, hydroboric acid, nitric acid, sulfuric acid, and phosphoric acid. Salts of organic acids include, e.g., formic acid, acetic acid, fumaric acid, oxalic acid, tartaric acid, maleic acid, lactic acid, citric acid, succinic acid, malic acid, methanesulfonic acid, benzenesulfonic acid, and p-toluenesulfonic acid. Salts of basic amino acids include, e.g., arginine, lysine and ornithine. Acidic amino acids include, e.g., aspartic acid and glutamic acid.

The term "subject," as used herein, refers to any animal that can experience the beneficial effects of the formulations and methods embodied herein. Thus, a compound of Formula I, a pharmaceutically acceptable salt thereof, or mixtures of any two or more thereof may be administered to any animal that can experience the beneficial effects of the compound in accordance with the methods of treating cancer provided herein. Preferably, the animal is a mammal, and in particular a human, although it is not intended to be so limited. Examples of other suitable animals include, but are not limited to, rats, mice, monkeys, dogs, cats, cattle, horses, pigs, sheep, and the like.

"Treating," as used herein, refers to an alleviation of symptoms associated with a disorder or disease, or halt or slowing of further progression or worsening of those symptoms, or prevention or prophylaxis of the disease or disorder. For example, within the context of cancer, successful treatment may include an alleviation of symptoms, or halting or slowing of the progression of the disease, as measured by a reduction in the growth rate of a tumor, a halt in the growth of the tumor, a reduction in the size of a tumor, partial or complete remission of the cancer, or increased survival rate or clinical benefit.

"Solvate," as used herein, refers to an association of a solvent with a compound, in the crystalline form. The solvent association is typically due to the use of the solvent in the synthesis, crystallization, and/or recrystallization of the compound.

"Hydrate," as used herein, refers to an association of water with a compound, in the crystalline form. The water association is typically due to the use of the water in the synthesis, crystallization, and/or recrystallization of the compound, and may also be a result of the hygroscopic nature of the compound.

"About," as used herein in conjunction with a stated numerical value, refers to a value within ±10% of the stated numerical value.

As used herein, and unless otherwise specified, "a" or "an" refers to "one or more."

It will be readily understood by those of skill in the art, that some materials identified below as belonging to a category such as a surfactant, a polymeric carrier, or as a coating material may fall into one or more of those categories, although not listed as part of the other categories. For example, hydroxypropyl cellulose is a polymeric carrier in some embodiments, and/or may be used as a coating for a capsule or tablet in other embodiments. Other such materials belonging in more than one category, but listed in only one category, will be readily identified by one of skill in the art.

Salts and compositions and formulations of salts of benzimidazolyl pyridyl ether compounds are provided in accordance with one aspect of the present invention. More specifically, the invention herein pertains to salts and formulations comprising salts of a compound of Formula I, and to methods for preparing and using such formulations. As used throughout this disclosure, Formula I refers to {1-methyl-5-[2-(5-trifluoromethyl-1H-imidazol-2-yl)-pyridin-4-yloxy]-1H-benzoimidazol-2-yl}-(4-trifluoromethyl-phenyl)amine, a compound having the structure:

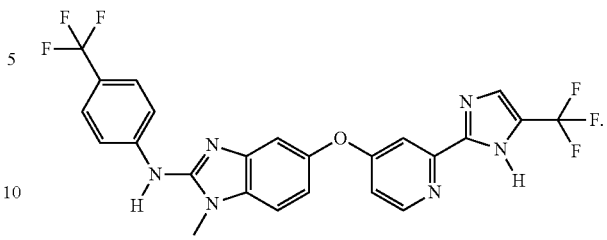

It will be understood by those of skill in the art, that a compound of Formula I, can also exist in the form of solvates and/or hydrates and that all such solvates and hydrates are encompassed by the compound and structure of Formula I.

It should also be understood that organic compounds according to the invention may exhibit the phenomenon of tautomerism. As drawings of a chemical structure can only represent one possible tautomeric form at a time, it should be understood that the compound of Formula I encompasses any tautomeric form of the drawn structure. For example, one possible tautomer of the compound of Formula I is shown below as Tautomer Ia:

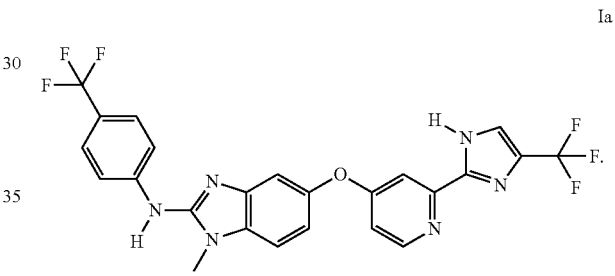

Those of skill in the art, will recognize and understand that the compound of Formula I, and tautomers thereof, may also exist in solvate and/or hydrate forms and are also encompassed by the compound and/or structure of Formula I. Likewise, pharmaceutically acceptable salts of the compound of Formula also encompass the corresponding solvates and/or hydrates of the pharmaceutically acceptable salts of the compound of Formula I.

Salts and Formulations of Salts

In one aspect, the present invention provides salts of benzimidazolyl pyridyl ethers such as {1-methyl-5-[2-(5-trifluoromethyl-1H-imidazol-2-yl)-pyridin-4-yloxy]-1H-benzoimidazol-2-yl}-(4-trifluoromethyl-phenyl)amine. Salts of the compound of Formula I include acetate, tosylate, succinate, lactate, malate, sulfate, maleate, citrate, hydrochloride, phosphate, and methanesulfonate salts. In some embodiments, the salts are selected from {1-methyl-5-[2-(5-trifluoromethyl-1H-imidazol-2-yl)-pyridin-4-yloxy]-1H-benzoimidazol-2-yl}-(4-trifluoromethyl-phenyl)amine hydrochloride, {1-methyl-5-[2-(5-trifluoromethyl-1H-imidazol-2-yl)-pyridin-4-yloxy]-1H-benzoimidazol-2-yl}-(4-trifluoromethyl-phenyl)amine ethanesulfonate or {1-methyl-5-[2-(5-trifluoromethyl-1H-imidazol-2-yl)-pyridin-4-yloxy]-1H-benzoimidazol-2-yl}-(4-trifluoromethyl-phenyl)amine methanesulfonate, or {1-methyl-5-[2-(5-trifluoromethyl-1H-imidazol-2-yl)-pyridin-4-yloxy]-1H-benzoimidazol-2-yl}-(4-trifluoromethyl-phenyl)amine maleate. In some embodiments, the salts of the compound of Formula I are selected to have a minimum aqueous solubility of at least 2, 5, or 10 times or more than the free base. For example, such salts can have a solubility of at least about 0.058 mg/mL in distilled water.

In another aspect, the invention provides a composition or formulation comprising a pharmaceutically acceptable acid salt of {1-methyl-5-[2-(5-trifluoromethyl-1H-imidazol-2-yl)-pyridin-4-yloxy]-1H-benzoimidazol-2-yl}-(4-trifluoromethyl-phenyl)amine and a surfactant. The compositions and formulations described herein may be solids or liquids and generally have improved solubilities and dissolution rates over the unformulated free base or salts of the compound of Formula I.

While many pharmaceutically acceptable acids may be used as the cognate acid in acid salts of the invention, acids having a pKa of about 4.7 or less than 4.7 are particularly useful. While not intending to be so limited, because the apparent pKa of the compound of Formula I is believed to be about 4.7, acids with pKas at or below this level can improve the solubility of the compound. Thus, in some embodiments of compositions or formulations of the invention, the cognate acid of the acid salt has a pKa of from about 4.7 about −6. In other embodiments, the cognate acid of the acid salt has a pKa of from about 4 to about −6, about 3 to about −6, about 2 to about −6, about 4.7 to about −5, about 4.7 to about −4, about 4.7 to about −3, about 4 to about −5, about 4 to about −4, about 4 to about −3, about 3 to about −6, and about 3 to about −5, about 3 to about −3, and about 2.5 to about −3.

Suitable cognate acids of the acid salts of the invention include a carboxylic acid, carbonic acid, acid salt of an amino acid, ascorbic acid, isoascorbic acid, amino acid, polyamino acid, alkanesulfonic acid, inorganic acid, polymeric acid, or a mixture of any two or more thereof. For example, the cognate acid of the acid salt can be malic acid, citric acid, tartaric acid, oxalic acid, succinic acid, adipic acid, fumaric acid, acetic acid, formic acid, lactic acid, maleic acid, phthalic acids, creatinine hydrochloride, pyridoxine hydrochloride, thiamine hydrochloride, cysteine hydrochloride, glycine hydrochloride, cystine dihydrochloride, peptides, toluene sulfonic acid, methanesulfonic acid, ethanesulfonic acid, phosphoric acid, phosphonic acid, orthophosphoric acid, hydrochloric acid, sulfonic acid, sulfuric acid, nitric acid, sodium metabisulfite, potassium phosphate monobasic, polyphosphoric acid, polyvinylsulfuric acid, polyvinylsulfonic acid, or a mixture of any two or more thereof. In some embodiments, the cognate acid of the acid salt is selected from the group consisting of acetic acid, toluene sulfonic acid, succinic acid, lactic acid, malic acid, sulfuric acid, maleic acid, citric acid, hydrochloric acid and methanesulfonic acid.

Compositions and formulations of the invention may include a range of amounts of the pharmaceutically acceptable acid salt of {1-methyl-5-[2-(5-trifluoromethyl-1H-imidazol-2-yl)-pyridin-4-yloxy]-1H-benzoimidazol-2-yl}-(4-trifluoromethyl-phenyl)amine. For example, the amount of this salt can range from about 0.1 wt % to about 80 wt %, from about 0.5 wt % to about 70 wt %, from about 1 wt % to about 50 wt % or from about 1 wt % to about 25 wt % based upon the total weight of the composition. The amount of active pharmaceutical ingredient in compositions and formulations of the invention varies with the intended application, and it is well within the skill of those in the art to determine the appropriate amount for any particular application based on the disclosure herein.

Any suitable surfactant can be used in compositions and formulations of the invention. The surfactant is typically used to improve wetting of API and excipients, and prevent the acid salts of the invention, especially salts of the compound of Formula I existing in ionization equilibrium with its free base in aqueous media, from precipitating upon dilution in aqueous solution, although the invention is not intending to be so limited. Thus, in some embodiments, the surfactant has an HLB value of about 8 or higher than 8. For example the surfactant may have an HLB value of from about 8 to about 40 or higher, from about 8 to about 40, 18, 16, 14, 12, or 10. In other embodiments, the surfactant may have an HLB value of about 9, 10, 11, or 12 to about 20, or from about 9 to about 18, about 9 to about 15, about 9 to about 16, about 10 to about 18, about 10 to about 16, or about 10 to about 15.

Surfactants that may be used in compositions or formulations of the invention include polyoxyethylene castor oil compounds, polyoxyethylene mono- and di-fatty, acid esters, mixtures of polyoxyethylene mono- and di-esters of $C_8$-$C_{22}$ fatty acids and glyceryl mono-, di-, and tri-esters of $C_8$-$C_{22}$ fatty acids (e.g., sold under trade names Gelucire 44/14, Gelucire 50/13, Gelucire 53/10 by Gattefosse), d-α-tocopheryl polyethylene glycol 1000 succinate, polyoxyethylene-polyoxypropylene copolymers, polyoxyethylene sorbitan fatty acid esters, polyoxyethylene alkyl ethers, sodium dioctyl sulfosuccinate, sodium lauryl sulfate, sorbitan fatty acid esters, sugar fatty acid esters, or a mixture of any two or more thereof. In some embodiments, the surfactant can be polyoxyl 35 castor oil, polyoxyl 40 hydrogenated castor oil, polyoxyl 60 hydrogenated castor oil, polysorbate 20, polysorbate 40, polysorbate 60, polysorbate 80, polyoxyl 40 stearate, polyoxyl 150 stearate, polyoxyl 150 distearate, d-α-tocopheryl polyethylene glycol 1000 succinate, poloxamer 124, poloxamer 188, poloxamer 407, sorbitan monolauryl ester, sorbitan monopalmityl ester, sorbitan monostearyl ester, or a mixture of any two or more thereof. In still other embodiments, the surfactant can be d-α-tocopheryl polyethylene glycol 1000 succinate, poloxamer 188, Gelucire 44/14, Gelucire 50/13, Gelucire 53/10 or a mixture of any two or more thereof.

Compositions and formulations of the invention may include a range of amounts of the surfactant. For example, the amount of the surfactant can range from about 0.01 wt % to about 60 wt %, from about 0.1 wt % to about 50 wt % or from about 1 wt % to about 25 wt % based upon the total weight of the composition. The amount of surfactant in compositions and formulations of the invention varies with the intended application, and it is well within the skill of those in the art to determine the appropriate amount for any particular application based on the disclosure herein.

Compositions and formulations of the invention are characterized by having improved solubility and dissolution rates in aqueous solutions over the free base or a salt of compound of Formula I. For example, in some embodiments, the composition or formulation including a surfactant has a solubility of at least about 0.058 mg/mL in distilled water or simulated gastric fluid. In other embodiments, the composition or formulation including a surfactant has a solubility of at least about 0.092, 0.096, 0.46 or 0.78 mg/mL in distilled water or in simulated gastric fluid. In still other embodiments the composition or formulation has a solubility of at least about 0.9, 1.0, 1.2, 1.4, 1.6, 1.8, 2.0, or 2.3 mg/mL in distilled water or simulated gastric fluid. In some embodiments, at least 90 wt % of a sample of a composition or formulation of the invention containing the equivalent of about 100 mg of {1-methyl-5-[2-(5-trifluoromethyl-1H-imidazol-2-yl)-pyridin-4-yloxy]-1H-benzoimidazol-2-yl}-(4-trifluoromethyl-phenyl)amine dissolves in 900 mL of simulated gastric fluid at 37±0.5° C. in about 90 minutes or less than 90 minutes. In other embodiments, at least 90 wt % the sample dissolves in about 60 minutes or less than 60 minutes, or in about 30 minutes or less than 30 minutes. In other embodiments at least 95, 98 or 99 wt % of the sample dissolves in about 90, 60 or 30 minutes or in less than 90, 60 or 30 minutes.

Compositions and formulations of the invention may further include additional excipients such as a carrier, e.g., a polymeric carrier or a non-polymeric carrier. The carriers of the invention are polymers or other materials suitable for use as a medium to deliver a drug substance. Thus, e.g., a carrier may be an adsorbent carrier, disintegrant, binder, lubricant, glidant, or diluent that will facilitate delivery of a drug substance to a subject. Suitable polymeric carriers include cross-linked povidone; cross-linked sodium carboxymethylcellulose; cross-linked β-cyclodextrin polymer; cross-linked dextran; cross-linked carbomer; hydroxyethylcellulose; hydroxypropylmethylcellulose; hydroxypropylcellulose; hydroxypropylmethylcellulose-acetate succinate; cellulose acetate phthalate; α-, β-, or γ-cyclodextrin; polyanionic-β-cyclodextrins, sulfobutylether-7-β-cyclodextrin; acrylic resins selected from homopolymers of acrylic acid, homopolymers of acrylic acid derivatives, copolymers of acrylic acid and acrylic acid derivatives; methacrylic acid copolymers, polymethacrylate polymers, poly(methacrylic acid-methyl methacrylate), poly(methacrylic acid-ethyl acrylate), ammonio methacrylate copolymer, poly(ethyl acrylate-methylmethacrylate-trimethylammonioethyl methacrylate chloride), poly(ethyl acrylate-methyl methacrylate), polyvinyl alcohol with an average molecular weight of from about 20,000 to about 200,000 g/mol, polyvinylpyrrolidine/vinylacetate, povidone with an average molecular weight of from about 2,500 to about 300,000 g/mol, polyethylene glycol; starch; sodium starch glycolate; microcrystalline cellulose; silicified microcrystalline cellulose; polyethylene glycol; or a mixture of any two or more thereof. Suitable non-polymeric carriers include lactose; sorbitol; mannitol; calcium carbonate; dicalcium phosphate; aluminum magnesium silicate; talc; aluminum silicate; bentonite; silicon dioxide; or a mixture of any two or more thereof.

Compositions and formulations of the invention may be contained within a capsule or tablet. In capsules or tablets, the total mass of the pharmaceutically acceptable acid salt of {1-methyl-5-[2-(5-trifluoromethyl-1H-imidazol-2-yl)-pyridin-4-yloxy]-1H-benzoimidazol-2-yl}-(4-trifluoromethyl-phenyl)amine may, e.g., range from about 0.01 mg to about 400 mg, from about 0.1 to about 400 mg, from about 1 to about 400 mg, from about 1 to about 100 mg, from about 1 to about 50 mg, from about 1 to about 25 mg, from about 1 to about 10 mg or from 1 to about 5 mg. In other embodiments, the total mass of the compound of Formula I, a pharmaceutically acceptable salt thereof, or a mixture of any two or more thereof, contained within the capsule or tablet, ranges from about 0.01 mg to about 10 mg, from about 0.1 mg to about 10 mg, from about 0.01 mg to about 5 mg, from about 0.1 mg to about 5 mg. In still other embodiments, the total mass of the compound of Formula I, a pharmaceutically acceptable salt thereof, or a mixture of any two or more thereof, contained within the capsule or tablet, ranges from about 0.01 mg to about 100 mg, from about 0.1 mg to about 100 mg, from about 0.01 to about 50 mg, from about 0.1 to about 50 mg, from about 0.01 mg to about 25 mg, or from about 0.1 mg to about 25 mg.

Compositions and formulations embodied herein may also include pharmaceutically acceptable additives such as an antioxidant, a coloring agent, a flavoring agent, a preservative, a sweetener, or a mixture of any two or more thereof. Antioxidants suitable for use in the embodied formulations include, but are not limited to, ascorbic acid, ascorbyl palmitate, butylated hydroxyanisole, butylated hydroxytoluene, ethylenediaminetetraacetic acid, salts of ethylenediaminetetraacetic acid, propyl gallate, sodium metabisulfite, vitamin E, esters of Vitamin E, or a mixture of any two or more thereof. Preservatives suitable fix use in the embodied formulations include, but are not limited to, butylparaben, calcium sorbate, ethylparaben, methylparaben, monothioglycerol, potassium sorbate, propylparaben, sodium benzoate, sodium sorbate, sorbic acid, or a mixture of any two or more thereof. Sweeteners suitable for use in the embodied formulations include, but are not limited to, aspartame, glycyrrhizin monoammonium glycyrrhizinate, saccharin, saccharin calcium, saccharin sodium, sugar, sucralose, or a mixture of any two or more thereof. Flavoring agents suitable for use in the embodied formulations include, but are not limited to, citric acid, menthol, peppermint oil, sodium citrate, vanillin, ethyl vanillin, or a mixture of any two or more thereof. Coloring agents suitable for use in the embodied formulations include, but are not limited to, FD&C blue #1, FD&C blue #2, FD&C green #3, FD&C red #3, FD&C red #4, FD&C yellow #5, FD&C yellow #6, D&C blue #4, D&C green #5, D&C green #6, D&C orange #4, D&C orange #5, iron oxides, or a mixture of any two or more thereof.

In some embodiments, formulations of the present disclosure are solid solutions, or dispersions. In some such embodiments, formulations are contained within a capsule or a tablet. In some embodiments, the capsule is a hard shell capsule, a hard gelatin capsule, a soft gelatin capsule, natural pullulan capsule, or a hydroxypropyl methylcellulose shell capsule. In some embodiments, the total mass of the pharmaceutically acceptable acid salt of the compound of Formula I, in the capsule or tablet ranges from about 1 mg to about 400 mg. In some embodiments, the capsule or tablet is coated with polymer or gelatin, or is encapsulated within a gelatin sheath. The capsule may be hard shell capsule and may further have a band-sealed head section and a body section. The capsules, or tablets may be encapsulated within a gelatin sheath and the gelatin sheath may further include a pharmaceutically acceptable coloring agent, a sweetener, an opacifier, or a mixture of any two or more thereof. Optionally, capsules or tablets may be coated with a sweetener, a cellulose polymer, a polymethacrylate polymer, polyvinyl acetate phthalate, a gelatin, or a mixture of any two or more. In embodiments where cellulose polymers are used to coat a capsule or tablet, the cellulose polymer may be selected from methylcellulose, hydroxyethylcellulose, hydroxyethylmethylcellulose, hydroxypropyl cellulose, hydroxypropylmethylcellulose, ethylcellulose, cellulose acetate phthalate, or a mixture of any two or more thereof. In embodiments where a polymethacrylate polymer is used to coat a capsule or tablet, the polymethacrylate polymer may be selected from methacrylic acid copolymers, poly(methacrylic acid-methylmethacrylate), poly(methacrylic acid-ethylacrylate), ammonio methacrylate copolymer, poly(ethyl acrylate-methylmethacrylate-trimethylammonioethyl methacrylate chloride), poly(ethyl acrylate-methyl methacrylate), or a mixture of any two or more thereof.

Methods

In another aspect, methods for producing compositions and formulations described herein are provided. Thus, in some embodiments, the methods comprise combining a pharmaceutically acceptable acid salt of {1-methyl-5-[2-(5-trifluoromethyl-1H-imidazol-2-yl)-pyridin-4-yloxy]-1H-benzoimidazol-2-yl}-(4-trifluoromethyl-phenyl)amine and a surfactant to provide a composition or formulation as described herein. In other embodiments, the methods include combining a compound, {1-methyl-5-[2-(5-trifluoromethyl-1H-imidazol-2-yl)-pyridin-4-yloxy]-1H-benzoimidazol-2-yl}-(4-trifluoromethyl-phenyl)amine, a pharmaceutically acceptable acid, and a surfactant to provide the compositions and formulations of the invention described herein. For example, the compound, acid, and surfactant can be combined by mixing the compound and acid together to provide a salt of the compound, and subsequently mixing the salt of the compound with the surfactant to provide a composition or formulation as described herein. The salt may be in the form of a paste which may be dried and/or further processed prior to being mixed with the surfactant.

Alternatively, the compound and the acid can be mixed by dissolving the compound and the acid in a formulation aid such as an organic solvent to form the salt of the compound. The salt can be isolated from the organic solvent by, e.g., precipitation or removal of the organic solvent through evaporation or under reduced pressure, or by any suitable technique known to those skilled in the art, including combinations of two or more such techniques. Organic solvents suitable for use as formulation aids include ketones, alcohols, ethers, esters or a mixture of any two or more thereof. Exemplary organic solvents include acetone, tetrahydrofuran, methanol, ethanol, isopropanol and mixtures of any two or more. In some embodiments, the formulation aid is removed by spray-drying, and/or spray coating the formulation onto a pharmaceutically acceptable carrier to form a solid dispersion, and/or grinding the solid dispersion to form granules. In some embodiments, granules formed by such methods have a size of less than 250 µm. In some embodiments, the granules are screened (i.e., passed through a screen) to provide a uniform size distribution for filling a capsule with the granules. In embodiments where tablets are prepared instead of capsules, the granules are mixed with excipients(s) as described below to form a second mixture, which is then pressed into the tablet.

In some embodiments of methods of the invention, the amount of the pharmaceutically acceptable acid salt of {1-methyl-5-[2-(5-trifluoromethyl-1H-imidazol-2-yl)-pyridin-4-yloxy]-1H-benzoimidazol-2-yl}-(4-trifluoromethylphenyl)amine ranges from about 0.1 wt % to about 80 wt %, from about 0.5 wt % to about 70 wt %, from about 1 wt % to about 50 wt % or from about 1 wt % to about 25 wt % based upon the total weight of the composition.

All methods of preparing compositions and formulations of the invention may further include combining a polymeric or non-polymeric carrier with the acid salt and the surfactant. Any of the methods may further include combining an antioxidant, a coloring agent, a cyclodextrin, a flavoring agent, a preservative, a sweetener, or a mixture of any two or more thereof with the acid salt and the surfactant. Suitable acids, surfactants, polymeric and non-polymeric carriers, antioxidants, coloring agents, cyclodextrins, flavoring agents, preservatives, sweeteners, and other excipients are as described throughout this disclosure. In some embodiments of methods of the invention, the amount of surfactant ranges from about 0.01 wt % to about 60 wt %, from about 0.1 wt % to about 50 wt % or from about 1 wt % to about 25 wt % based upon the total weight of the composition. In some embodiments, the antioxidant is present at up to about 1 wt % based upon the total weight of the formulation. In other embodiments, the sweetener is present at up to about 2 wt % based upon the total weight of the formulation. In other embodiments, the flavoring agent is present at up to about 2 wt % based upon the total weight of the formulation.

In some embodiments, the methods further include forming at least one capsule or tablet with the formulation. In such capsules or tablets, the total mass of the pharmaceutically acceptable acid salt of the compound of Formula ranges from about 0.01 mg to about 400 mg, from about 0.1 to about 400 mg, from about 1 to about 400 mg, from about 1 to about 100 mg, from about 1 to about 50 mg, from about 1 to about 25 mg, from about 1 to about 10 mg or from 1 to about 5 mg. In other embodiments, the total mass of the compound of Formula I, a pharmaceutically acceptable salt thereof, or a mixture of any two or more thereof, contained within the capsule or tablet, ranges from about 0.01 mg to about 10 mg, from about 0.1 mg to about 10 mg, from about 0.01 mg to about 5 mg, from about 0.1 mg to about 5 mg. In still other embodiments, the total mass of the compound of Formula I, a pharmaceutically acceptable salt thereof, or a mixture of any two or more thereof, contained within the capsule or tablet, ranges from about 0.01 mg to about 100 mg, from about 0.1 mg to about 100 mg, from about 0.01 to about 50 mg, from about 0.1 to about 50 mg, from about 0.01 mg to about 25 mg, or from about 0.1 mg to about 25 mg. In some such methods where a capsule is formed the capsule may be, but is not limited to, those capsules as described above.

Sealing of capsules may be accomplished by many methods known to those of skill in the art. In some embodiments, sealing methods include spraying a mist of alcohol and water solution onto an inside lip of the head section to cause the hard shell capsule to form an adhesive gel, placing the head section in position over the body section to form the capsule, exposing the capsule to an elevated temperature of from about 35° C. to about 55° C., and allowing the adhesive gel to set. In other embodiments, the capsules are band-sealed.

Tablets formed by the disclosed methods are, in some embodiments, formed using a conventional tablet press or molding calendar with a pair of counter-rotating, chilled molding rolls. Thus, methods of preparing solid formulations include, but are not limited to hot melt methods as described above and below in the examples, and solvent dissolution/evaporation methods as described above and below in the examples.

Packaging

Pharmaceutical packagings are ubiquitous throughout the industry and most are well-suited to the formulations disclosed. Pharmaceutical packagings and/or containers for inventive formulations may include a storage vessel for one or more capsules, tablets, cachets, or lozenges of formulations embodied herein. Such embodiments of storage vessels include those made of any of a number of pharmaceutically compatible polymers, glasses and metals, including, e.g., high density polyethylene. Disclosed pharmaceutical packagings include blister packaging, with at least one capsule, tablet, cachet, or lozenge of the formulation(s) disclosed herein. Further, such storage vessels may include a cotton or rayon coil and/or a heat induction seal. Suitable packaging is widely known to those of skill in the art and is not limiting of the broader aspects of this disclosure.

Methods of Treating

In another aspect, methods for treating cancer, inhibiting angiogenesis, and/or inhibiting RAF kinase in a subject are provided. In some embodiments, the method comprises administering to a subject in need of a cancer treatment, a composition or formulation as described herein. In some embodiments, the method comprises administering to a subject in need of an angiogenesis inhibitor, a formulation embodied herein. In other embodiments, methods comprise administering to a subject in need of an RAF kinase inhibitor, a formulation embodied herein. The formulations are typically administered in an amount sufficient to provide a $C_{max}$ of about 0.1 to about 5,000 ng/mL, from about 0.1 to 1,000 ng/mL, about 0.1 to 500 ng/mL, or about 1 to 150 ng/mL and/or an $AUC_{0 \to \infty}$ of about 0.01 to about 5,000 µg*min/mL, about 1 to about 5,000 µg*min/mL, about 1 to about 2,000

μg*min/mL, or about 1 to about 1,000 μg*min/mL of the compound of Formula I, a pharmaceutically acceptable salt thereof, or a mixture of any two or more thereof, in the subject's plasma. However, while exemplified dosage rates were used in controlled studies, administered dosages of API in a subject may range from about 0.01 mg to about 50 mg per kilogram body mass of the subject, including from about 0.01 mg/kg to about 25, from about 0.01 mg/kg to about 10 mg/kg, or from about 0.01 mg/kg to about 1, 2, 3, 4, or 5 mg/kg.

Treatment regimens and methods of treating a subject with a compound of Formula I, a pharmaceutically acceptable salt thereof, or a mixture of any two or more thereof, are provided. In some embodiments, methods of treating cancer and/or inhibiting angiogenesis in a subject include administering a formulation of a compound of Formula I, a pharmaceutically acceptable salt thereof, or a mixture of any two or more thereof, once, twice, three times, four, or more times daily. In some embodiments, administration of such formulations includes treatment cycles of administering such formulations daily for 7, 14, 21, or 28 days, followed by 7 or 14 days without administration of the formulation. In other embodiments, the treatment cycle includes administration of the formulation daily for 7 days, followed by 7 days without administration of the compound. In some embodiments, the treatment cycle is repeated one or more times.

As noted above, a pharmaceutically acceptable salt of the compound of Formula I may be used for the treatment of various cancers in a subject. In some embodiments, the cancer to be treated includes, but is not limited to, bladder, breast, brain, head and neck, liver, biliary tract, carcinomas, acute and chronic lymphoid leukemias, acute and chronic myelogenous leukemias, chronic myelomonocytic leukemias, colorectal, gastric, gastrointestinal stromal, glioma, lymphomas, melanomas, multiple myeloma, myeloproliferative diseases, neuroendocrine, lung, pancreatic, prostate, renal cell, sarcomas, and thyroid cancers.

In any formulation, method, or packaging of the present invention it is contemplated where capsules are so provided, tablets may also be provided and where tablets are so provided, capsules may also be provided. Where tablets and/or capsules are so provided, cachets and/or lozenges may also be provided.

One skilled in the art will readily realize that all ranges discussed can and do necessarily also describe all subranges therein for all purposes and that all such subranges also form part and parcel of this invention. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present embodiments, thus generally described, will be understood more readily by reference to the following examples, which are provided by way of illustration and are not intended to be limiting of the present invention.

Experimental

Nomenclature for the compounds was provided using ACD Name version 5.07 software (Nov. 14, 2001) available from Advanced Chemistry Development, Inc., ChemInnovation NamExpert+Nomenclator™ brand software available from ChemInnovation Software, Inc., and AutoNom version 2.2 available in the ChemOffice® Ultra software package version 7.0 available from CambridgeSoft Corporation (Cambridge, Mass.). Some of the compounds and starting materials were named using standard IUPAC nomenclature.

Various starting materials may be obtained from commercial sources and prepared by methods known to one of skill in the art.

Example 1

Synthesis of {1-methyl-5-[2-(5-trifluoromethyl-1H-imidazol-2-yl)-pyridin-4-yloxy]-1H-benzoimidazol-2-yl}-(4-trifluoromethyl-phenyl)amine (Formula I)

Step 1

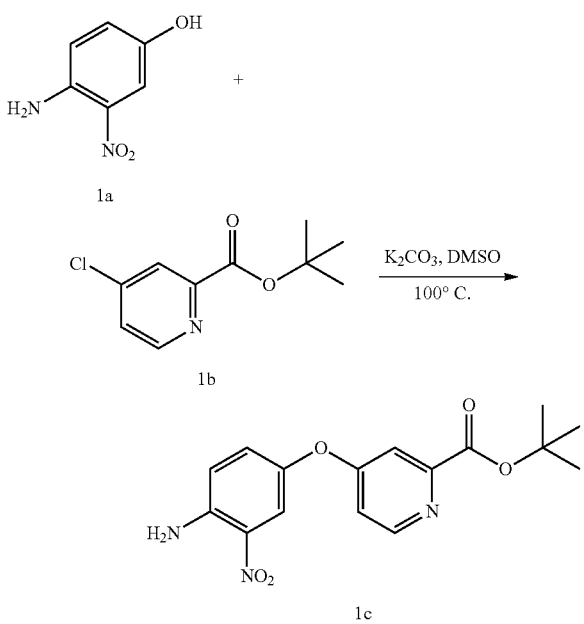

A 500 mL three-neck flask was fitted with a mechanical stirrer and charged with $K_2CO_3$ (4.15 g, 30 mmol). The vessel was sealed, evacuated, and flame dried. The apparatus was allowed to cool to rt and purged with argon. To the reaction flask was added 4-amino-3-nitrophenol 1a (3.08 g, 20 mmol), tert-butyl 4-chloropyridine-2-carboxylate 1b (5.2 g, 24 mmol) and dry DMSO (30 mL). The resulting mixture was stirred vigorously and heated to 100° C. for ~14 h. The reaction was poured over iced phosphate buffer (pH=7) and the reaction flask was rinsed well with MTBE and water. The combined biphasic mixture was filtered through Celite (>2 cm pad). The layers were partitioned and separated and the aqueous phase was extracted with MTBE (3×100 ml). The combined organic layers were washed with water (5×100 mL), dried ($MgSO_4$), and evaporated. The crude residue was adsorbed onto $SiO_2$, and purified by flash chromatography (4:1, 2:1, 1:1 hexanes/EtOAc) to furnish 4.92 g (14.9 mmol, 74% yield) of 1c as a yellow brown solid. $^1H$ NMR (300 MHz, $CDCl_3$) δ 8.58 (d, J=5.8 Hz, 1 H), 7.90 (d, J=2.8 Hz, 1 H), 7.56 (d, J=2.5 Hz, 1 H), 7.17 (dd, J=2.8, 8.8 Hz, 1 H), 6.94 (dd, J=2.8, 5.8, Hz, 1 H), 6.91 (d, J=9.1 Hz, 1 H), 6.15 (br s, 2 H), 1.62 (s, 9 H); $^{13}C$ NMR (75 MHz, $CDCl_3$) δ 165.8, 164.0, 151.8, 151.5, 143.4, 143.2, 131.5, 129.8, 121.0, 118.0, 114.2, 113.1, 83.0, 28.4; mp 163-166° C.

Step 2

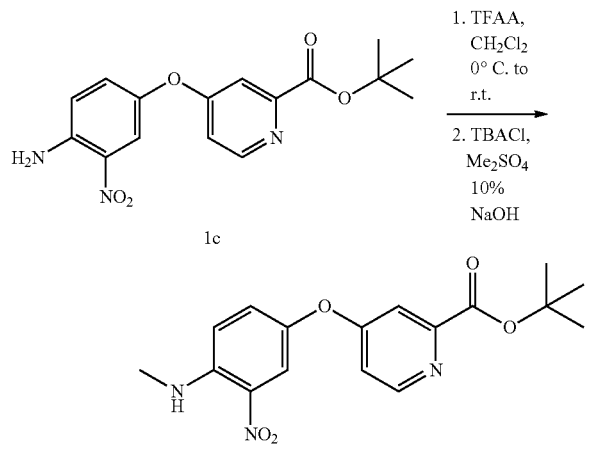

To a solution of 1c (5.62 g, 17 mmol) in CH$_2$Cl$_2$ (85 mL) at 0° C. was added TFAA (2.4 mL, 3.6 g, 17 mmol). The cooling bath was then removed and the reaction maintained at rt for 2 h. The reaction was cooled to 0° C. and TBACl (2.5 g, 8.5 mmol), Me$_2$SO$_4$ (3.2 mL, 4.3 g 34 mmol), and 10% NaOH (34 mL) were added. The resulting mixture was stirred vigorously for 4 h at rt. The reaction was diluted with water and the resulting layers were partitioned and separated. The aqueous phase was extracted with CH$_2$Cl$_2$ (3×100 mL), and the combined organic layers were washed with brine (2×100 mL), dried (MgSO$_4$), and evaporated. The crude residue was adsorbed onto silica gel and purified by flash chromatography (4:1, 2:1, 1:1, 1:2 hexanes/EtOAc) to give 4.5 g (13.0 mmol, 76%) of 1d as a yellow-orange solid. $^1$H NMR (300 MHz, CDCl$_3$) δ 8.54 (d, J=5.5 Hz, 1H), 8.04 (br d, J=4.7 Hz, 1 H), 7.93 (d, J=2.8 Hz, 1 H), 7.53 (d, J=2.5 Hz, 1 H), 7.25 (app dd, J=2.8, 9.1 Hz, 1 H), 6.91 (m, 2 H), 3.04 (d, J=4.9 Hz, 3 H), 1.59 (s, 9 H); $^{13}$C NMR (75 MHz, CDCl$_3$) δ 165.9, 164.1, 151.5, 144.7, 142.1, 130.4, 118.8, 115.5, 114.1, 112.9, 82.9, 30.4, 28.5; mp 187-189° C.

Step 3

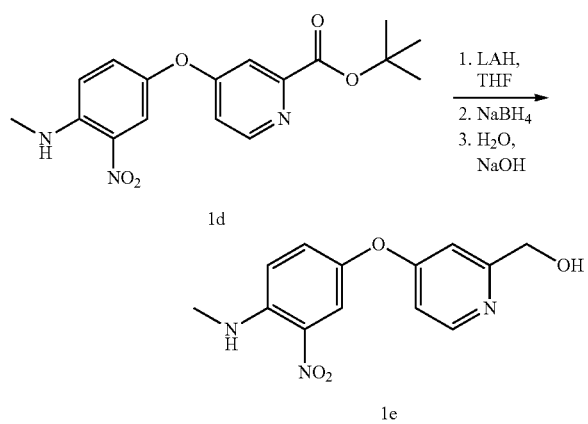

A flame dried 500 mL three necked round bottom flask purged with N$_2$ was charged with LAH (3.0 g, 75 mmol) and dry THF (240 mL). The resulting suspension was cooled to 0° C. and 1d (20.7 g, 60 mmol) was slowly added white keeping the internal reaction temperature under 5° C. The reaction mixture was stirred at 0° C. for 2 h followed by stirring at rt overnight. NaBH$_4$ (2.27 g, 60 mmol) was added and the reaction mixture was stirred for an additional hour at rt. After the reaction was judged complete, the reaction mixture was treated with successive dropwise addition of water (3 mL), 15% NaOH (3 mL), and water (9 mL). The resulting mixture was filtered through Celite, and the remaining solids were washed with EtOAc and MeOH. The combined organic portions were evaporated and the resulting crude residue was adsorbed onto SiO$_2$ and purified by flash chromatography (97:3 CH$_2$Cl$_2$/MeOH) to afford 7.63 g (27.7 mmol, 46%) of a red-orange solid as 1e. $^1$H NMR (300 MHz, CDCl$_3$) δ 8.40 (d, J=5.5 Hz, 1 H), 8.05 (br s, 1H), 7.96 (d, J=2.75 Hz, 1 H), 7.29 (d, J=2.75 Hz, 1 H), 6.92 (d, J=9.35 Hz, 1 H), 6.75 (m, 2 H), 4.68 (s, 2 H), 3.07 (d, J=5.23 Hz, 3 H).

Step 4

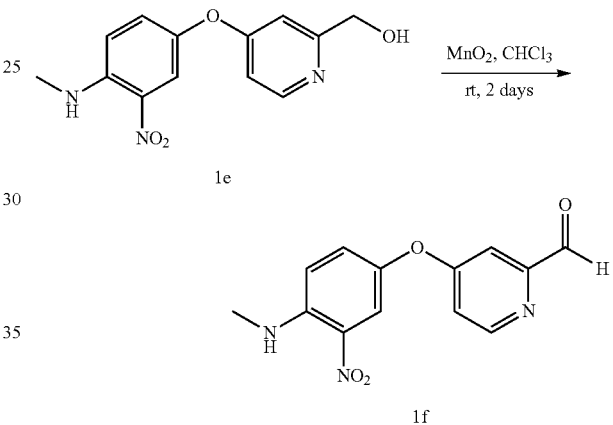

A 100 mL round bottom flask was charged with 1e (1.38 g, 5.0 mmol), MnO$_2$ (6.52 g, 75 mmol) and CHCl$_3$ (20 mL). The resulting suspension stirred at rt for 2 d. The reaction mixture was filtered through Celite, and the remaining solids were washed successively with CHCl$_3$ and EtOH. The combined organic portions were evaporated, absorbed onto silica gel, and purified by flash chromatography (98:2 CH$_2$Cl$_2$/MeOH) to give 790 mg (2.89 mmol, 58%) of an orange solid as 1f. $^1$H NMR (300 MHz, CDCl$_3$) δ 10.01 (s, 1 H), 8.64 (d, J=5.5 Hz, 1 H), 8.09 (br s, 1 H), 7.96 (d, J=2.75 Hz, 1 H), 7.37 (d, J=2.48 Hz, 1 H), 7.29 (d, J=2.75 Hz, 1 H), 7.08 (dd, J=2.47, 5.5 Hz, 1 H), 6.94 (d, J=9.35 Hz, 1 H), 3.08 (d, J=5.23 Hz, 3 H).

Step 5

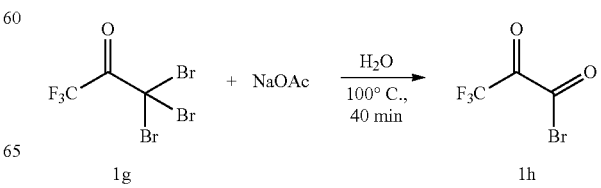

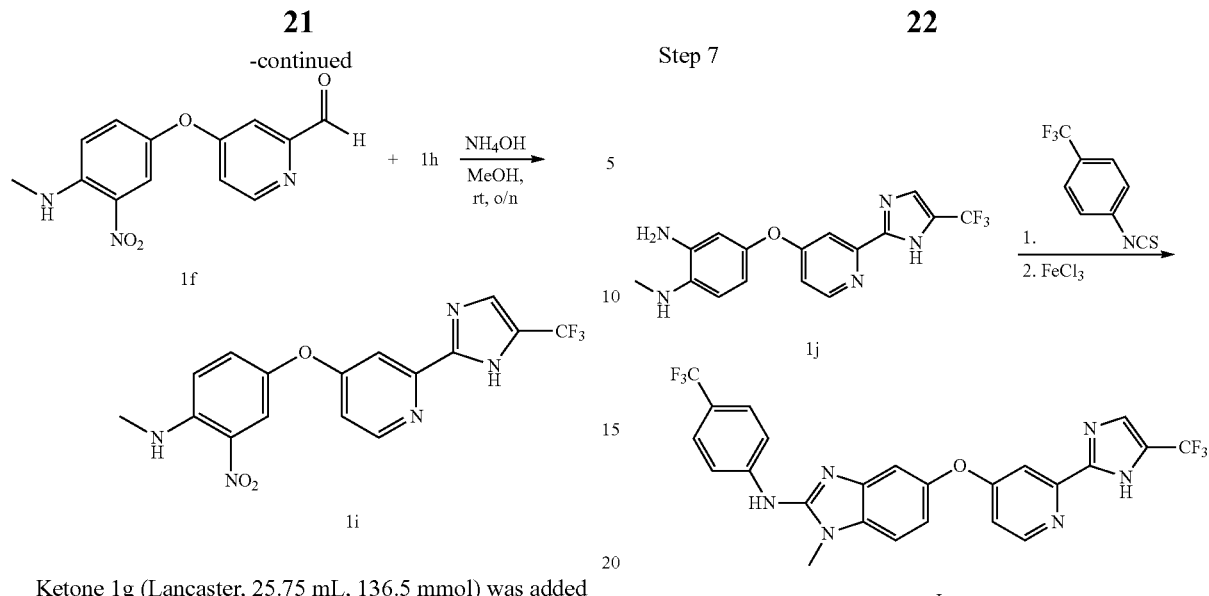

Step 7

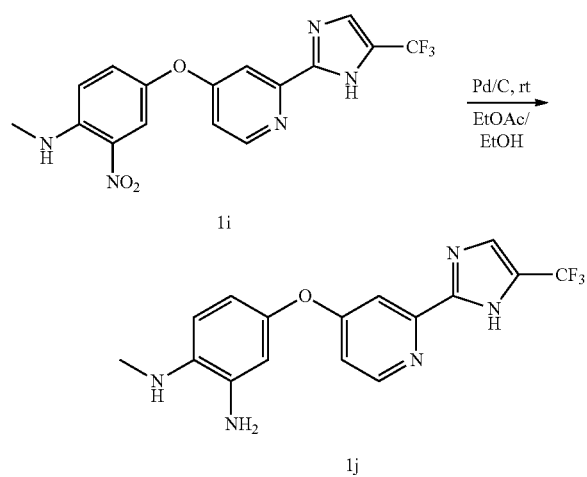

Ketone 1g (Lancaster, 25.75 mL, 136.5 mmol) was added to a solution of sodium acetate (NaOAc) (22.4 g, 273 mmol) in $H_2O$ (60 mL) and the resulting solution heated to 100° C. for 10 min. After cooling to rt, the solution of 1h was added to a suspension of 1f (25 g, 91 mmol) in $NH_4OH$ (150 mL) and MeOH (450 mL). The resulting mixture was stirred at rt overnight. TLC (95:5 $CH_2Cl_2$/MeOH) showed complete consumption of 1f. The crude product was concentrated into an aqueous slurry, and partitioned with saturated $Na_2CO_3$ and $CH_2Cl_2$. The aqueous phase was extracted three times with $CH_2Cl_2$, and the combined organics washed with brine, dried with $MgSO_4$, and concentrated to give 31.6 g of 1i (83 mmol) as an orange solid (91% yield). No further purification was required.

Step 6

A slurry of 1i (45.76 g, 120 mmol) MeOH (220 mL) and EtOAc (200 mL) was sparged with $N_2$ for 20 min, and then charged with a suspension of 10% Pd/C (12.77 g, 120 mmol) in MeOH (60 mL). The reaction was purged with $H_2$ and maintained under a $H_2$ atmosphere for 2 days. The reaction was filtered through a pad of Celite and the collected solids were washed successively with MeOH and EtOAc. The combined organic filtrates were evaporated, and the resulting solid was azeotroped with $CH_2Cl_2$ and dried overnight, under vacuum, to give 40.17 g (115 mmol) of 1j as a tan powder (96% yield). LCMS m/z 336.1 ($MH^+$), $t_R$=1.81 min.

4-(Trifluoromethyl)phenyl isothiocyanate (23.37 g, 115 mmol) was added to a stirring solution of 1j (40.17 g, 115 mmol) in MeOH (460 mL) at rt. The reaction was maintained at rt for 16 h. After the reaction was judged complete, a solution of $FeCl_3$ (20.52 g, 126.5 mmol) in MeOH (50 mL) was added to the reaction and the resulting mixture was stirred at rt overnight. The crude reaction mixture was added to a 3 L separatory funnel containing EtOAc (750 mL) and water (750 mL). The layers were separated, and the aqueous phase was extracted with EtOAc (aqueous phase saved). The organic layers were combined, washed with saturated aqueous $Na_2CO_3$ solution, water, and brine, then dried ($MgSO_4$), and concentrated. The saved aqueous phase was made basic (pH=10) by addition of saturated aqueous $Na_2CO_3$ solution and the resulting slurry was added to a 3 L separatory funnel containing EtOAc (500 mL). The mixture was agitated and the resulting emulsion was filtered through filter paper, and the layers were then separated and the aqueous phase was extracted with EtOAc (2×500 mL). The organic layers were combined, washed with brine, then dried ($MgSO_4$), added to previously extracted material and concentrated. The combined product was triturated with $CH_2Cl_2$ (500 mL), adsorbed onto $SiO_2$ and purified by flash chromatography. A final trituration of material with $CH_2Cl_2$ produced the compound of Formula I as a pure, white solid. LCMS m/z 519.1 (MH+); $^1H$ NMR (300 MHz, $CDCl_3$) δ 8.44 (d, J=5.5 Hz, 1 H), 7.75 (d, J=8.8 Hz, 2H), 7.61 (dd, J=2.2, 8.5 Hz, 1 H), 7.59 (d, J=8.8 Hz, 2 H), 7.56 (d, J=2.5 Hz, 1 H), 7.38 (app d, J=8.5 Hz, 1 H), 7.23 (d, J=1.9 Hz, 1 H), 6.96 (dd, J=2.2, 8.5 Hz, 1 H), 6.93 (dd, J=2.5, 5.5 Hz, 1 H), 3.76 (s, 3 H); LCMS m/z=519.0, $t_R$=2.57 min ($MH^+$); Anal. calc'd for $C_{24}H_{16}F_6N_6O$: C, 55.6; H, 3.11, N, 16.21. Found: C, 55.81; H, 3.43; N, 16.42; mp: 217-220° C. (dec.).

Example 2

Aqueous Solubility of API

The aqueous solubility of the compound of Formula I was assessed as a function of pH. Solubility of the compound of Formula I was determined using the shake flask method. The following aqueous solutions of hydrochloric acid (HCl) were prepared: 100, 33.3, 11.1, 3.7, 1.2, 0.4, and 0 mM. The following aqueous solutions of sodium hydroxide (NaOH) were prepared: 1.2 and 0.4 mM. The ionic strength of each of these solutions was adjusted to 0.15 using potassium chloride. Excess amounts of the compound of Formula I were added to a 1 mL aliquot of each of the above solutions in 1.5-mL polypropylene tubes. The tubes were agitated at room temperature for 5 days before analysis. On the day of analysis, the tubes were centrifuged at 15,000 revolutions per minute (rpm) using a microcentrifuge at 22° C. for 20 minutes. The concentration of compound of Formula I in the supernatant was measured by HPLC. The pH of the supernatant was measured using an Orion pH meter, which was calibrated before use.

The aqueous solubility of the compound at various pHs is listed in the following Table 1. As shown, {1-methyl-5-[2-(5-trifluoromethyl-1H-imidazol-2-yl)-pyridin-4-yloxy]-1H-benzoimidazol-2-yl}-(4-trifluoromethyl-phenyl)amine is practically insoluble in water.

TABLE 1

Aqueous Solubility of API as a function of pH

| pH | Solubility (mg/mL) |
| --- | --- |
| 1.36 | 0.7094 |
| 2.19 | 0.1253 |
| 3.75 | 0.0019 |
| 5.78 | 0.0004 |
| 10.13 | 0.0003 |
| 11.00 | 0.0003 |

Example 3

Preparation of Salts of the Compound of Formula I

The compound of Formula I was prepared as described in Example 1. Hydrochloric acid (HCl), sodium hydroxide (NaOH), acetic acid, lactic acid, succinic acid, malic acid, citric acid, ethanesulfonic acid, maleic acid, methanesulfonic acid, toluenesulfonic acid, phosphoric acid, and sulfuric acid were all United States Pharmacopoeia-National Formulary (USP-NF) grade or ACS grade.

Conversion of the compound of Formula I to various salt forms was accomplished via an acid-base reaction in an organic liquid medium followed by a slow evaporation of the organic solvent, except for the mesylate, esylate, and maleate salts which were prepared as described in Example 6, below. An accurately weighed amount of the compound of Formula I (443.4 mg) was dissolved in a total of 8.39 mL of a solvent mixture composed of 7.39 mL acetone and 1 mL methanol. 0.567 mL aliquots of this solution were placed in 1.5 mL polypropylene tubes to yield 30 mg of the solid compound of Formula I upon drying. Tubes containing the compound of Formula I were left overnight in the chemical fume hood to air-dry. Equimolar amounts of the respective cognate acids were added to the vials from acetonitrile (ACN) solutions of the acids (1 mL of 57.86 mM acid solutions). The resulting converted salt suspensions were agitated overnight at room temperature. The following day, the salt suspensions were dissolved by the addition of 0.5 mL of methanol, agitated for 1 hr and allowed to air dry in the chemical fume hood. Upon drying, the solid salt materials were subjected to microscopic examination and aqueous solubility testing. Microscopic examination was performed with a polarized light microscope to assess the crystalline nature of the materials. The salt solubility studies were performed by adding excess solid salt material to 1 mL of deionized water in 1.5 mL polypropylene tubes and agitating for 48 hr at room temperature. The tubes were then centrifuged at 15,000 rpm for 20 min at 22° C. in a microcentrifuge. Concentrations of the various salts in the supernatant were measured by HPLC and the pH of each was measured and recorded. The supernatant was then discarded and the pellets were resuspended in deionized water for another solubility determination.

HPLC analyses were performed using Waters Alliance™ 2695 Separation Module equipped with Waters 2996 Diode Array Detector. Separation was performed using 4.6×150 mm Synergi Hydro-RP C18 reversed phase HPLC column at temperature of 35° C. Mobile phase conditions consisted of 0.1% Trifluoroacetic acid (TFA) in water (Solvent A) and 0.1% TFA in ACN (Solvent B). Flow was maintained at 1 mL/min with the linear gradient elution shown in Table 2.

TABLE 2

HPLC Solvent Gradient

| Time (min.) | % Solvent A | % Solvent B |
| --- | --- | --- |
| 0 | 95 | 5 |
| 40 | 40 | 60 |
| 45 | 95 | 5 |
| 50 | 95 | 5 |

Quantitative analyses of the compound of Formula I were performed at 254 nm wavelength using an external standard curve.

In an attempt to increase the aqueous solubility and dissolution rate of compound of Formula I, initially ten acids were screened for their ability to form salts with the compound of Formula I free base. The acids included relatively weak acids such as acetic and lactic acids. They also included strong acids such as sulfuric, hydrochloric, toluenesulfonic, and methanesulfonic acids as shown in Table 3.

The crystalline nature of each of the collected salts was assessed microscopically using a polarized light microscope. As shown in Table 3, microscopic examination of collected salts indicated that some salts were crystalline and the others were mixtures of crystalline and amorphous phases. When the salts were evaluated for their equilibrium aqueous solubility, they exhibited low levels of solubility and low pH of the saturated solutions. Given the very weakly basic nature of the compound of Formula I, it was assumed that the salts dissociated in aqueous media and mostly reverted back to the free base and the respective free acid counter ions during the equilibration process. The residual solids in these aqueous suspensions were, therefore, collected, and their aqueous solubility was evaluated in freshly added deionized water. As shown in Table 3, the obtained solubility is consistent with that of the free base confirming that the salts reverted back to the free base upon contact with water. The observed behavior of compound of Formula I salts is not an unexpected one given the weak basicity and the low intrinsic aqueous solubility of the compound. A closer inspection of the pH-solubility profile of compound of Formula I in Table 1 reveals that the compound did not attain maximum solubility even at the lowest pH tested, i.e., pH 1.36. This indicates that the pH of a saturated solution of a salt of Formula I is lower than 1.36. Salts that require a low pH to attain the saturated solution are known to be unstable and to revert back to the free base when in contact with aqueous media (Serajuddin A. T. M. and Pudipeddi M. *Salt Selection Strategies*. In Handbook of Pharmaceutical Salts Properties, Selection, and Use. Stahl P. H. and Wernauth C. G. (Eds). 2002, Wiley-VCH).

TABLE 3

Salts of the Compound of Formula I

| Salt | Crystallinity[1] | Solubility[2] (mg/mL) | pH[3] | Solubility of Residual Solid[4] (mg/mL) |
|---|---|---|---|---|
| Free Base | Crystalline | 0.004 | 5.235 | 0.009 |
| Acetate | Crystalline | 0.006 | 3.892 | 0.002 |
| Tosylate | Mixture | 0.011 | 2.91 | 0.006 |
| Succinate | Crystalline | 0.018 | 2.552 | 0.003 |
| Lactate | Crystalline | 0.058 | 2.668 | 0.004 |
| Malate | Mixture | 0.092 | 2.918 | 0.001 |
| Sulfate | Mixture | 0.096 | 2.517 | 0.021 |
| Maleate | Crystalline | 0.096 | 2.415 | 0.017 |
| Citrate | Mixture | 0.155 | 2.405 | 0.006 |
| Hydrochloride | Crystalline | 0.457 | 2.079 | 0.010 |
| Methanesulfonate | Crystalline | 0.774 | 1.992 | 0.004 |

[1]Crystallinity was assessed by polarized light microscope;
[2]Aqueous solubility of salts collected from organic solvent;
[3]pH of the saturated aqueous solutions;
[4]Aqueous solubility of residual solids collected from the saturated aqueous solutions

Example 4

Capsule Solid Dosage Formulations

The API, a weak base, exhibits increased aqueous solubility as the pH of the medium is lowered. Thus, the aqueous solubility of API may be improved through its conversion into an acidic salt form. Two acids, i.e., hydrochloric acid and methanesulfonic acid were chosen as prototypical acids to convert API free base into its salt forms.

The compound of Formula I was prepared as described in Example 1. d-α-Tocopheryl polyethylene glycol 1000 succinate (TPGS; Eastman Chemicals), Gelucire 44/14 (Gattefosse), Poloxamer 188 (Pluronic F-68; Sigma chemicals), and Polyoxyl 40 stearate (Myrj 52-S, Uniqema) were selected as the surfactants to aid as wetting agents and aqueous solubility enhancers for API free base. These surfactants were chosen because they have higher HLB values and are solids at ambient temperatures. Crospovidone (BASF), sodium starch glycolate, and Starch 1500 (Colorcon) were chosen as potential disintegrants. Avicel PH 101 (FMC), Povidone K30 (BASF), and fumed silica (Degussa Corporation) were used as a bulking agent, a binder, and a glidant, respectively. PEG 8000, oleic acid, methanesulfonic acid, hydrochloric acid, and acetone were used as received.

Formulation Preparation

The formulations were prepared using three approaches: (1) by directly employing a harvested salt form of Formula, (2) utilizing solubility enhancers coupled with in-situ salt formation and (2) utilizing solubility enhancers alone. The formulations prepared using these approaches are summarized in Tables 4 and 5, respectively.

1. Use of Harvested and In-Situ Salt Formation to Prepare Various Formulations

TABLE 4

Formulations using various salt formation processes

| | Composition, %, w/w | | | | |
|---|---|---|---|---|---|
| Ingredients | #1 | #2 | #3 | #4 | #5 |
| API (free base) | 27.15 | 27.14 | 23.48 | 22.99 | 23.89 |
| Acetone[1] | 250 | 250 | 0 | 0 | 0 |
| HCl 37% | 9.10 | 0 | 0 | 24.45 | 5.43 |
| Methanesulfonic acid | 0 | 9.05 | 23.53 | 0 | 0 |
| PEG 8000 | 0 | 0 | 0 | 0 | 41.27 |
| Avicel PH101 | 21.67 | 21.80 | 18.35 | 18.18 | 0 |
| Poloxamer 188 | 36.09 | 36.14 | 30.62 | 30.56 | 18.19 |
| TPGS | 4.60 | 4.54 | 4.01 | 3.82 | 9.41 |
| Fumed silica | 1.39 | 1.32 | 0 | 0 | 1.81 |
| TOTAL | 100 | 100 | 100 | 100 | 100 |
| Capsule fill weight, mg | 368 | 368 | 425 | 435 | 419 |
| Target API dose, mg | 100 | 100 | 100 | 100 | 100 |

[1]Pharmaceutical aid, removed after preparation.

Formulations #1 and #2 in Table 4, which employed harvested (i.e., pre-isolated) salt forms, were prepared as follows: 3 g of API was dissolved in 25 g of acetone and mixed with either 1 g of 37% HCl or 1 g of methanesulfonic acid (about twice the equimolar ratio to API). The clear yellow solution so formed was set aside undisturbed for several hours until the salt form of the API completely precipitated from the solution. The precipitate was collected by filtration and dried. The salt form was blended with the rest of the excipients (except fumed silica) and wet granulated with about 1.5 mL of water in a grinder. The granulation was then dried in a laminar flow hood at room temperature for more than 24 hours. The dried granulation was blended with fumed silica in the grinder. The resultant granulation was stored in a 10 mL scintillation glass vial until needed for further use. Approximately 368 mg of the granulation (i.e., equivalent to 100 mg API free base dose) were filled into size 00 hard gelatin capsules.

Formulations #3 and #4 in Table 4, which are salt forms prepared in situ, were prepared as follows: 3 g of API was mixed thoroughly with either about 3 g of 37% HCl or about 3 g of methanesulfonic acid (about six times the equimolar ratio to API) using a spatula to form a homogeneous paste. The paste was set aside overnight. The paste was mixed with the other excipients and granulated with about 1.5 mL of water in a in a grinder. The resultant granulation was dried and stored in a 10 mL scintillation glass vial until needed for further use. Approximately 435 mg of the granulation (i.e., equivalent to 100 mg API free base dose) were filled into size 00 hard gelatin capsules.

Formulation #5 in Table 4 was prepared with in-situ hydrochloride salt as follows: API was mixed with PEG 8000 at approximately 60° C. to form a paste. The paste was mixed with 37% HCl solution. Poloxamer 188 and TPGS were added to the hot melt and mixed thoroughly until a homogeneous molten mass was formed. The molten mass was spread onto an Aluminum foil as thin sheets and allowed to cool. The sheets were cut, milled in a grinder, and mixed with fumed silica to form granules. Approximately 420 mg of the granules (i.e., equivalent to 100 mg API free base dose) were filled into size 00 hard gelatin capsules.

2. Comparative Examples

Wet Granulation with Surfactants as Solubility Enhancers

TABLE 5

Formulations using solubility enhancers

| | Composition, %, w/w | | |
|---|---|---|---|
| Ingredients | #6 | #7 | #8 |
| API free base | 11.4 | 12.8 | 20 |
| PEG 8000 | 38.6 | 49.4 | 0 |
| Gelucire 44/14 | 0 | 0 | 39.7 |
| Polyoxyl 40 stearate | 30.6 | 0 | 0 |
| TPGS | 0 | 9.9 | 0 |
| Sodium starch glycolate | 0 | 20 | 0 |
| Crospovidone | 15.5 | 0 | 40.3 |
| Oleic acid | 0 | 7.9 | 0 |
| PVP K30 | 3.9 | 0 | 0 |
| TOTAL | 100 | 100 | 100 |
| Capsule fill weight, mg | 877 | 781 | 500 |
| Target API dose, mg | 100 | 100 | 100 |

Formulation prototypes #6, #7, and #8 in Table 5 were prepared as follows:

All ingredients designated for each formulation prototype were blended and granulated in a grinder using 2-2.5 mL water. The granulation was dried and filled into size 00 hard gelatin capsules so that each capsule contained 100 mg API free base.

Dissolution Methodology

The dissolution test was performed in 900 mL simulated gastric fluid (SGF) at 37±0.5° C. using a USP type 2 dissolution apparatus. The dissolution test was (performed at 100 rpm paddle rotation speed. Sinkers were used to prevent the capsules from floating. Approximately 2.5 mL samples were withdrawn through a coarse inline filter at 15, 30, 45, 60, 90, and 120 minute intervals. The samples were further filtered through 0.45 µm disk filters and assayed using an HPLC procedure. The dissolution profiles of the formulations prepared using the three approaches are summarized in Table 6.

TABLE 6

Dissolution profiles of API from capsule formulations in SGF media

| Time, | % API released | | | | | | | |
|---|---|---|---|---|---|---|---|---|
| min | #1 | #2 | #3 | #4 | #5 | #6 | #7 | #8 |
| 15 | 74.1 | 68.3 | 94.6 | 81.5 | 96.6 | 53.3 | 61.9 | 7.9 |
| 30 | 90.4 | 91.3 | 100.3 | 96.9 | 99.9 | 66.4 | 83.3 | 17.4 |
| 45 | 99.7 | 96.8 | 99.4 | 98.6 | 99.6 | 70.7 | 93.2 | 27.0 |
| 60 | 99.8 | 99.7 | 99.0 | 102.0 | 99.9 | 72.9 | 97.6 | 34.9 |
| 90 | 100 | 100 | 100 | 100 | 100 | 75.1 | 100 | 43.8 |

Formulations #1-5 were prepared using solubility enhancers and in-situ salt formation approach;
Formulations #6-8 were prepared using solubility enhancers only approach In an approach that couples solubility enhancers with the in-situ salt formation approach, salt formation was achieved either by dissolving both API and an acid in a suitable solvent, e.g., acetone or molten PEG 8000 (e.g., #1, #2, and #5) and harvesting the salt that precipitates out of solution for further processing or by directly mixing both components together in the acid and wet-granulating the blend with a granulation fluid (e.g., #3 and #4). The results suggest that the dissolution profiles were not influenced by either the type and equimolar ratio of acid used (hydrochloric acid versus methanesulfonic acid) or the method or process employed in generating the in-situ salt (solvent precipitation versus direct granulation in the presence of an acid) to prepare the granules. The resultant capsule provided a very rapid dissolution, i.e. ≧90% API was released from the capsules in ≦30 minutes. In contrast, the formulations prepared utilizing the solubility enhancers alone approach (e.g., #6, #7, and #8) provided a less than optimal dissolution front the capsules.

Example 5

Tablet and Capsule Solid Dosage Formulations

Method 1: Wet Granulation. In wet granulation methods, API and an acid are mixed at a molar ratio of 1:1 to 1:6, with or without deionized water, in a mixer to form the granulating fluid. The other inactive ingredients are then wet granulated using the granulating fluid. The resultant wet mixture is dried and milled to give uniform granules. Additional excipients can be added to the granules to produce a final blend. The final blend is filled into two-piece gelatin or HPMC capsules. The final blend may optionally be compressed into tablets. The tablet or capsule can be further coated to modify its release profile, to improve its appearance/taste, and/or to protect the product from the storage environment.

Formulation 9

Sodium starch glycolate, poloxamer 188, and microcrystalline cellulose are dry blended in a Key International KG5 granulator. API is dissolved in 5% hydrochloric acid in a glass beaker and transferred into the KG5 as the granulation fluid. The granulation is mixed at a 400 rpm impeller speed and a 2,000 rpm chopper speed for 1 minute. The resultant granules are dried in an oven at 40° C. until the moisture content of the granulation is less than 10%. The granules formed are then screened through a #20 mesh screen. The screened granules are mixed with additional microcrystalline cellulose and sodium starch glycolate in a V blender for 5 minutes. Silicon dioxide and stearic acid are added to the blend and mixed for an additional 3 minutes. The final blend is then discharged from the V blender and compressed into tablets using a Carver press with a ½ inch round standard concave tooling.

Granule Formulation

| Ingredient | % w/w |
|---|---|
| API | 12.5 |
| Hydrochloric acid | 4.75 |
| Sodium starch glycolate | 20.0 |
| Poloxamer 188 | 10.0 |
| Microcrystalline cellulose | 52.75 |
| Total | 100 |

Tablet Formulation

| Ingredient | Amount per Tablet, mg |
| --- | --- |
| Granule Formulation | 400 mg (Equivalent to 50 mg API) |
| Microcrystalline cellulose | 158 mg |
| Sodium starch glycolate | 20 mg |
| Silicon dioxide | 10 mg |
| Stearic acid | 12 mg |
| Total Tablet weight | 600 mg |

Method 2: Wet Granulation. API and carriers are mixed in a high shear mixer or a planetary mixer. An acid solution is then added to the dry blend as the granulating fluid. The resultant wet mixture may then be further dried and milled to give uniform granules. Additional excipients can be added to the granules to produce a final blend. The final blend is then filled into a two-piece gelatin or HPMC capsule. The final blend may alternatively be compressed into a tablet. The tablet or capsule can be further coated to modify its release profile, to improve its appearance/taste, or to protect the product from the storage environment.

Formulation 10

API, crospovidone, poloxamer 188, and microcrystalline cellulose are dry blended in a PMS high-speed granulator. Diluted methanesulfonic acid is added to the dry blend to form wet granules. The resultant wet granules are dried in a GPCG fluid bed dryer and milled by a Comill to achieve desirable particle size range. The milled granules are mixed with sodium starch glycolate in a V blender for 5 minutes. Silicon dioxide and magnesium stearate are added to the blend and mixed for an additional 3 minutes. The final blend is discharged from the V blender and the granules are filled into a size 00 hard gelatin capsules using a MG2 encapsulation machine.

Granule Formulation

| Ingredient | % w/w |
| --- | --- |
| API | 12.5 |
| Methanesulfonic acid | 9.5 |
| Crospovidone | 20.0 |
| Poloxamer 188 | 10.0 |
| Microcrystalline cellulose | 48 |
| Total | 100 |

Capsule Formulation

| Ingredient | Amount per Capsule, mg |
| --- | --- |
| Granule Formulation | 400 mg (Equivalent to 50 mg API) |
| Sodium starch glycolate | 20 mg |
| Silicon dioxide | 10 mg |
| Magnesium stearate | 10 mg |
| Total Capsule fill weight | 440 mg |

Method 3: Wet Granulation. API and a surfactant are dissolved in a volatile organic solvent to form a solution. An acid is added to the solution to form a granulating fluid. A pharmaceutical carrier(s) and other inactive ingredients are then wet granulated using the granulating fluid. The resultant granules are dried and milled to give uniform size granules. Additional excipients may be added to the granules to produce a final blend. The final blend may be filled into a two-piece gelatin or HPMC capsule. The final blend may also be compressed into a tablet. The tablet or capsule may be further coated to modify its release profile, to improve its appearance/taste, and/or to protect the product from the storage environment.

Formulation 11

API and poloxamer 188 are dissolved in acetone, and sulfuric acid is added to form a granulating fluid. Crospovidone and microcrystalline cellulose are dry blended in a LB Bohle one-pot processor, and then wet granulated using the granulating fluid. The granulation is dried in the one-pot processor using vacuum and heat. The resultant granules are milled using a Comill to achieve the desirable particle size range. The milled granules are then mixed with croscarmellose sodium in a V blender for 5 minutes. Silicon dioxide and magnesium stearate are added to the blend and mixed for an additional 3 minutes. The final blend is discharged from the V blender and filled into a size 00 hard gelatin capsules using a MG2 encapsulation machine.

Granule Formulation

| Ingredient | % w/w |
| --- | --- |
| API | 12.5 |
| Sulfuric acid | 7.23 |
| Crospovidone | 20.0 |
| Poloxamer 188 | 10.0 |
| Microcrystalline cellulose | 50.27 |
| Total | 100 |

Capsule Formulation

| Ingredient | Amount per Capsule, mg |
| --- | --- |
| Granule Formulation | 400 mg (Equivalent to 50 mg API) |
| Croscarmellose sodium | 20 mg |
| Silicon dioxide | 10 mg |
| Magnesium stearate | 10 mg |
| Total Capsule fill weight | 440 mg |

Method 4: Spray-Drying. API and a surfactant are dissolved in a volatile organic solvent. A solid carrier is added to the solution to form a suspension followed by the addition of an acid to form a final suspension for spray-drying. Additional excipients can be added to the spray-dried granules to produce a final blend. The final blend can be filled into a two-piece gelatin or HPMC capsule. The final blend can also be compressed into a tablet. The tablet or capsule can be further coated to modify its release profile, to improve its appearance/taste, and/or to protect the product from the storage environment.

Formulation 12

API and poloxamer 188 are dissolved in acetone to form a solution. Crospovidone and microcrystalline cellulose are added to the solution to form a suspension. Sulfuric acid is added to the suspension and the resultant mixture is subjected to a Niro spray dryer. The resultant spray-dried granules are mixed with Croscarmellose sodium in a V blender for 5 minutes. Magnesium stearate is added to the blend and mixed for an additional 3 minutes. The final blend is discharged from the V blender and filled into a size 00 hard gelatin capsule using a MG2 encapsulation machine.

Spray-Dried Formulation

| Ingredient | % w/w |
| --- | --- |
| API | 12.5 |
| Sulfuric acid | 7.23 |
| Crospovidone | 30.0 |
| Poloxamer 188 | 10.0 |
| Microcrystalline cellulose | 40.27 |
| Total | 100 |

Capsule Formulation

| Ingredient | Amount per Capsule, mg |
| --- | --- |
| Granule Formulation | 400 mg (Equivalent to 50 mg API) |
| Croscarmellose sodium | 20 mg |
| Magnesium stearate | 10 mg |
| Total Capsule fill weight | 430 mg |

Method 5: Co-Precipitation. In co-precipitation methods, API and a surfactant are dissolved in a suitable volatile organic solvent. An insoluble solid carrier and an acid are then added to the solution to induce the co-precipitation of an in situ API salt with the surfactant and carrier. The solvent may then be removed by evaporation or by other appropriate methods. The resultant co-precipitate may be collected and dried. The particles so obtained are milled, sieved, and filled into two-piece hard capsules. Alternatively, these formulations may be further processed through milling, sieving, mixing with other excipients, and compressing into a tablet dosage formulation.

Formulation 13

API and poloxamer 188 are dissolved in acetone. Crospovidone and silicone dioxide are added to the solution to form a suspension. Cysteine hydrochloride is added to the suspension and the resultant mixture is subjected to a vacuum evaporator to remove the solvent. The resultant solid particles are then milled and mixed with croscarmellose sodium in a V blender for 5 minutes. Magnesium stearate is added to the blend and mixed for an additional 3 minutes. The final blend is discharged from the V blender and filled into a HPMC capsule using a Torpac™ Profill capsule filling system.

Co-Precipitation Formulation

| Ingredient | % w/w |
| --- | --- |
| API | 12.5 |
| Cysteine hydrochloride | 13.0 |
| Crospovidone | 30.0 |
| Poloxamer 188 | 10.0 |
| Silicon dioxide | 34.5 |
| Total | 100 |

Capsule Formulation

| Ingredient | Amount per Capsule, mg |
| --- | --- |
| Granule Formulation | 400 mg (Equivalent to 50 mg API) |
| Croscarmellose sodium | 20 mg |
| Magnesium stearate | 10 mg |
| Total Capsule fill weight | 430 mg |

Any of a number of appropriate apparatuses are available to assist in blending, extrusion, sizing, encapsulation, sealing, filling, pressing, and other processes in preparing pharmaceutical formulations. Various types of two-piece hard capsules include, but are not limited to, two-piece HGCs, HPMC capsules, and natural pullulan capsules. All such capsule shells may contain opacifiers such as talc and titanium dioxide, and colorants. Listed herein are numerous apparatuses that were used in the experimental processes, but are not intended to be limiting in any manner as many different makes, models, and manufacturers exist in the industrial setting. For example, blending equipment may include PK V-Blenders, cone tumble blenders, fluid bed granulators available from Glatt Air Techniques and Niro Pharma System, planetary mixers, and ribbon blenders. Hot melt extrusion equipment may include ZSE 18 HP; ZSE 27 HP; ZSE 40 HP; Micro 18; and Micro 27 co-rotating and counter-rotating twin screw extruders available from American Leistritz Extruder Corporation; single screw 19/20 DN, and twin screw DSE 25 & DSE 35 co-rotating & counter rotating twin screw extruders from Brabender Measurement & Control Systems; and Caleva Extruders Models 20, 40, and 100 available from Caleva Process Solutions Ltd. Sizing equipment may include Comil Sizers available from Quadro; Hammermill sizers available from Fitzpatrick; Oscillator sizers from a number of vendors. Hard capsule filling machines for fitting a molten mass such as the QUALICAPS F-40-LIQFILsuper40, QUALICAPS F-80-LIQFILsuper80, QUALICAPS F-120-LIQFILsuper120, QUALICAPS F-150-LIQFILsuper150, and the Capsugel CFS 1000 Capsule Filling and Seating Machine. Hard capsule seating machines such as the QUALICAPS S-40 HICAPSEAL and the QUALICAPS S-100 HICAPSEAL. Hard capsule filling machines for filling solid powders include the MG from MG2, the GKF from Bosch, and the Zanasi from IMA. Tablet press equipment available from Manesty, Fette, and Courtoy. Tablet coating equipment available from Niro Pharma Systems such as SIROCCO®; MULTI-PROCESSOR®; MP-MICRO®; STREA-1®; and MP-1 MULTI-PROCESSOR® and Glatt such as their fluid bed granular/dryer/coater.

Further Modifications of the Table Dosage Formulations. Tablet dosage forms may also be coated to improve appearance, elegance, and/or taste. In some cases, the tablet is coated with a sugar, cellulose polymer, and/or polymethacrylate polymer. Some examples of coating materials available commercially are under the trade names OPADRY®, SURELEASE®, AQUACOAT®, and EUDRAGIT®. The coating material may further contain a pharmaceutically acceptable coloring agent and/or a pharmaceutically acceptable opacifier, including but not limited to opacifiers such as titanium dioxide or talc. Alternatively, the tablet formulation may be coated with gelatin or encapsulated within a gelatin sheath. The gelatin sheath material may further contain a pharmaceutically acceptable coloring agent and/or a pharmaceutically acceptable opacifier.

Example 6

Salt Stability, Characterization, and Morphic Studies

Twenty acids were further screened for their ability to form salts with the API under different conditions than those described in Example 3 above. Three salts of the API were further investigated to determine their stability, chemical and physiochemical properties and morphology: mesylate, esylate and maleate. The ratio of acid to base (API) in these salts was 2:1 for mesylate and esylate salts and 1:1 for the maleate salt. The salts for these studies were prepared as follows.

Mesylate: Two equivalents of methanesulfonic acid were slowly added to 3 g of API in 20 mL of THF at room temperature. The resulting suspension was equilibrated for two hours before solids were collected by filtration. Solids were dried under vacuum at 50° C.

Esylate: Two equivalents of ethanesulfonic acid were slowly added to 3 g of API in 20 mL of THF at room temperature. The resulting suspension was equilibrated for two hours before solids were collected by filtration. Solids were dried under vacuum at 50° C.

Maleate: One equivalent of maleic acid was slowly added to 3 g of API in 20 mL of THF at room temperature. The resulting suspension was equilibrated for two hours before solids were collected by filtration. Solids were dried under vacuum at 50° C.

Instruments and Methodologies used in these studies were as follows.

Determination of Solubility

Excess solids were equilibrated in each solvent for over 24 hours at 25° C.±0.1. Concentration in aqueous supernatant was measured by UV and HPLC and concentrations in organic solvents by gravimetry.

Dissolution

The intrinsic dissolution rate measurements were carried out in 0.5 cm² VanKel die assemblies and a pellet pressure of 1 ton. The dissolution was measured using a Cary 50 spectrophotometer with a stirring rate of 200 rpm. The solution medium was held at 37° C. and measurements were made at 276 nm.

Hygroscopicity

Sorption/desorption isotherms were measured using VTI vapor sorption device (DVS-1). Measurements were carried out at 25° C.

Polymorphism Behavior

A suspension of 6 mg of drug substance in 300 μl of solvent is prepared. Samples are agitated for ≧24 hour at 22° C.±2° C. The solids are collected and investigated for changes.

HPLC Method

| Column: | Symmetry C18 (Waters), 3.5 μm, 3 × 150 mm |
|---|---|
| Mobile phase: | A = 0.1% TEA in water; B = acetonitrile |
| Gradient: | 20 to 100% B in 10 minutes |
| Flow rate: | 0.6 ml/min |
| Column temperature: | 40° C. |
| Amount injected: | about 1 μg API |
| Detection: | UV 254 nm |

Stability of the three salts with respect to color and degradation products were assessed under various conditions. Results are shown in Table 7, below. Chemical and physiochemical characteristics for the three salts were measured and are shown in Table 8. Results of morphology studies are shown in Table 9, below.

TABLE 7

Degradation Products (DP) (or Assay) and Appearance (Color, CL) of API Salts

| | API Salt Form | | | | | | | |
|---|---|---|---|---|---|---|---|---|
| | Free Base | | Mesylate | | Esylate | | Maleate | |
| Conditions Test Conditions | DP [%] | CL | DP [%] | CL | DP [%] | CL | DP [%] | CL |
| 0.1% solutions or suspensions, 1 week 80° C. (# or 50° C., or lower for unstable substances) | | | | | | | | |
| Unstressed | 0.6 | | 0.5 | | 0.5 | | 0.3 | |
| pH 1 | 1.4 | A | x | | x | | x | |
| pH 3 | 0.9 | A↓ | x | | x | | x | |
| pH 5 | 0.6 | A↓ | x | | x | | x | |
| pH 7 | 0.9 | A↓ | x | | x | | x | |
| pH 9 | 27.0 | A↓ | x | | x | | x | |
| pH 11 | >99 | A↓ | x | | x | | x | |
| Water | 0.6 | A↓ | 0.5 | A↓ | 0.4 | A↓ | 0.3 | A↓ |
| Methanol | 0.6 | A | 2.7 | A | 2.5 | A | 0.4 | A |
| Solid state, 1 week 80° C., tight container | | | | | | | | |
| Bulk (HPLC) | 0.6 | A | 0.5 | A | 0.5 | A | 0.7 | A |
| 1-2 weeks 50° C., tight container | | | | | | | | |
| 1% in mixture 1 | 0.7 | A | 0.5 | A | 0.5 | A | 0.4 | A |
| 1% in mixture 2 | 0.6 | A | 0.6 | A | 0.6 | A | 0.4 | A |
| Solid state, 1 week 80° C./75% r.h | | | | | | | | |
| Bulk (HPLC) | 0.6 | A | 0.8 | A | 0.6 | A | 0.4 | A |
| 1-2 weeks 50° C./75% r.h. | | | | | | | | |
| 1% in mixture 1 | 0.8 | A | 2 | A | 1.8 | A | 1.1 | A |
| 1% in mixture 2 | 0.5 | A | 1.2 | A | 0.8 | A | 0.5 | A |
| Xenon light (approx. 1200 kLuxh) | | | | | | | | |
| Bulk (HPLC) | 0.6 | A | 0.6 | A | 0.7 | A | 0.3 | A |
| Bulk corrosivity | | | | | | | | |
| 2 day 80 r.h. with steel coupon | x | | x | | x | | x | |

↓Suspension
\* Clear solution after stress test
— no change
A No change of color
B Slight discoloration
C Medium discoloration
D Strong discoloration
x test not performed
DPs are analyzed by HPLC (method see Appendix 2). They are calculated as area-% products or against external standard 1%).
DSC: Purity: 100% − (sum of byproducts and degradation products)
Compositions of the excipient mixtures (mass-%)
Mixture 1: Lactose 200 mesh/maize starch modified 1500 LM/Aerosil 200/Magnesium stearate 78.5:20:0.5:1 (m/m/m/m)
Mixture 2: Mannitol/Avicel PH 102/Cutina HR (57:38:5) (m/m/m)

TABLE 8

Chemical and Physicochemical Properties of API Salts

| Parameter | free base | | Mesylate | | Esylate | | Maleate | |
|---|---|---|---|---|---|---|---|---|
| Elemental analysis | calc. | found | calc. | found | calc. | found | calc. | found |
| % C | 55.6 | 53.86 | 43.95 | 42.82 | 45.54 | 44.0 | 53.00 | 52.84 |
| % H | 3.11 | 3.33 | 3.4 | 3.08 | 3.82 | 3.63 | 13.25 | 2.92 |
| % N | 16.21 | 15.82 | 11.83 | 11.43 | 11.38 | 10.78 | 13.25 | 13.22 |
| % O | 3.09 | | 15.76 | | 15.16 | | 16.17 | |
| % F | 21.99 | 20.68 | 16.04 | 14.85 | 15.43 | 13.85 | 17.97 | 16.89 |
| % S | | | 9.02 | 9.18 | 8.68 | 8.77 | | |

| Stoichiometry | | | | |
|---|---|---|---|---|
| NMR (acid:base) | NA | 2:1 | 2:1 | 1:1 |
| DSC-Purity | | | | |
| Heating rate 2° C./min (%) | Not applicable | Not applicable | Not applicable | Not applicable |
| HPLC-Purity (e.g. area-%) | 0.6 | 0.5 | 0.5 | 0.3 |
| Melting point (DTA) | 162.1° C. | 177.7° C. | 238.2° C. | 175.5° C. |
| Melting enthalpy (J/g) | Not applicable | Decomposes | Decomposes | Decomposes |

| pH of 1% solution or suspension | | | | |
|---|---|---|---|---|
| In water | 5.5 | 2.0 | 2.2 | 2.7 |

| Solubility (approx. at 25° C., mg/ml) (HPLC) | | | | |
|---|---|---|---|---|
| 0.1N HCl | 0.20 | 5.7 | 3.7 | 2.3 |
| Measured pH | | 1.3 | 1.4 | 1.4 |
| pH 3 | 0.00006 | 0.0005 | 0.0023 | 0.00015 |
| Measured pH | | 3.6 | | 3.4 |
| pH 4.5 | 0.00009 | 0.0001 | 0.0037 | 0.00003 |
| Water | 0.024 | 0.07 | 0.06 | 0.01 |
| Solid | No change | No change | No change | No change |
| Methanol | 11.4 | >50 | >50 | >50 |
| Acetonitrile | 5.2 | 4.0 | 2.1 | 4.7 |

| Thermogravimetry (weight loss in %) | | | | |
|---|---|---|---|---|
| Heating rate 20 K/min (%) | 3.3 | 1.3 | 2.1 | 0.11 |

| Intrinsic dissolution rate (mg min$^{-1}$ cm$^{-2}$) | | | | |
|---|---|---|---|---|
| HCl 0.1N | 0 | 0.056 | 0.06 | 0.03 |
| Water | 0 | 0.0024 | 0.0036 | 0.0076 |

TABLE 9

Morphic Properties of API Salts

| Parameter | free base | Mesylate | Esylate | Maleate |
|---|---|---|---|---|
| Thermal properties | | | | |
| As is | | | | |
| DSC | 162.1° C. | 177.7° C. | 250° C. | 175.7° C. |
| XRPD (crystallinity) | Crystalline | Crystalline | Crystalline | Crystalline |
| After heating and cooling- | | | | |
| DSC | Not measured | Decomposes | Decomposes | Decomposes |
| XRPD | Not measured | Not measured | Not measured | Not measured |
| Hygroscopicity | | | | |
| As is | | | | |
| Loss on drying by TG (%) | 3.3 | 1.3 | 2.1 | 0.11 |
| After 1 day at 95% r.h. | 0.1 | 13.0 | 14.9 | 1.1 |
| Loss on drying by TG (%) | Not measured | Not measured | Not measured | Not measured |
| DSC/XRPD | No change | No change | No change | No change |
| After 1 day at 80% r.h. | 0 | 4.0 | 5.3 | 0.8 |
| DSC/XRPD, TG (%) | Not measured | Not measured | Not measured | Not measured |

| Crystal modification after 24 hours equilibration | | | | |
|---|---|---|---|---|
| | DSC/XRPD/TG | DSC/XRPD/TG | DSC/XRPD/TG | DSC/XRPD/TG |
| Water | Change | Change | No change | No change |
| Ethanol | No change | No change | No change | No change |

TABLE 9-continued

| Morphic Properties of API Salts | | | | |
|---|---|---|---|---|
| 2-propanol | No change | No change | No change | No change |
| Ethyl acetate | No change | No change | No change | Change |
| Acetone | No change | No change | No change | Change |
| PEG400 | No change | No change | No change | Change |
| Acetonitrile | Change | No change | No change | Change |
| Methanol | No change | No change | No change | Change |
| Particle size Microscopy (μm) | 10-20 μm | <10 μm | <10 μm | <10 μm |
| Morphology | needles | needles | needles | needles |
| Effect of grinding | No change | No change | No change | No change |

Salt Formation. The API has low solubility in most organic solvents. Acetone and tetrahydrofuran provided the best results for salt crystallization. Salt formation with ethanesulfonic acid and methanesulfinic acid produces rapid precipitation causing the solution to thicken, and making workup a challenge. Salt formation with maleic acid provided better control of the crystallization process.

Aqueous Solubility. The API free base is nearly insoluble in water. Salt formation significantly improves aqueous solubility at all pH levels for the mesylate and esylate. Aqueous solubility for the maleate appears to be higher at low pH and lower in neutral conditions (>pH 3). Intrinsic dissolution data show that the dissolution rate at pH 1 is in the order of esylate=mesylate>maleate>>free base. In water, the order changes to maleate>esylate=mesylate>>free base.

Stability. The optimum pH for aqueous stability of API is 5. At lower pH, there is a small increase in degradation products and at higher pH (9 and 11) API decomposes. In methanol, the free base and maleate salt are stable while the esylate and mesylate show 2.7% impurities.

Figure 3A:
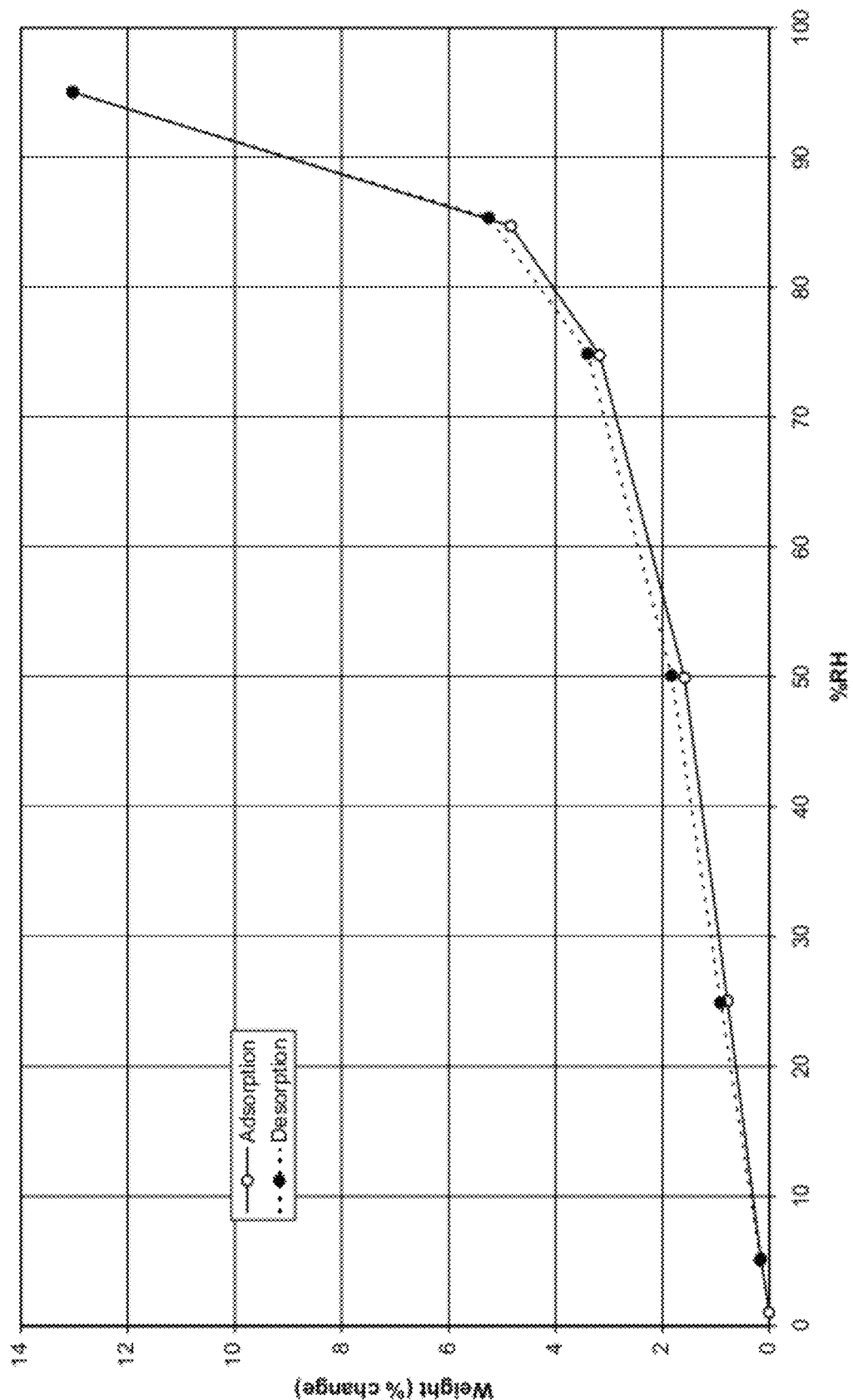
FIG. 3A: Sorption results for compound of Formula I as mesylate salt.
Figure 3B:
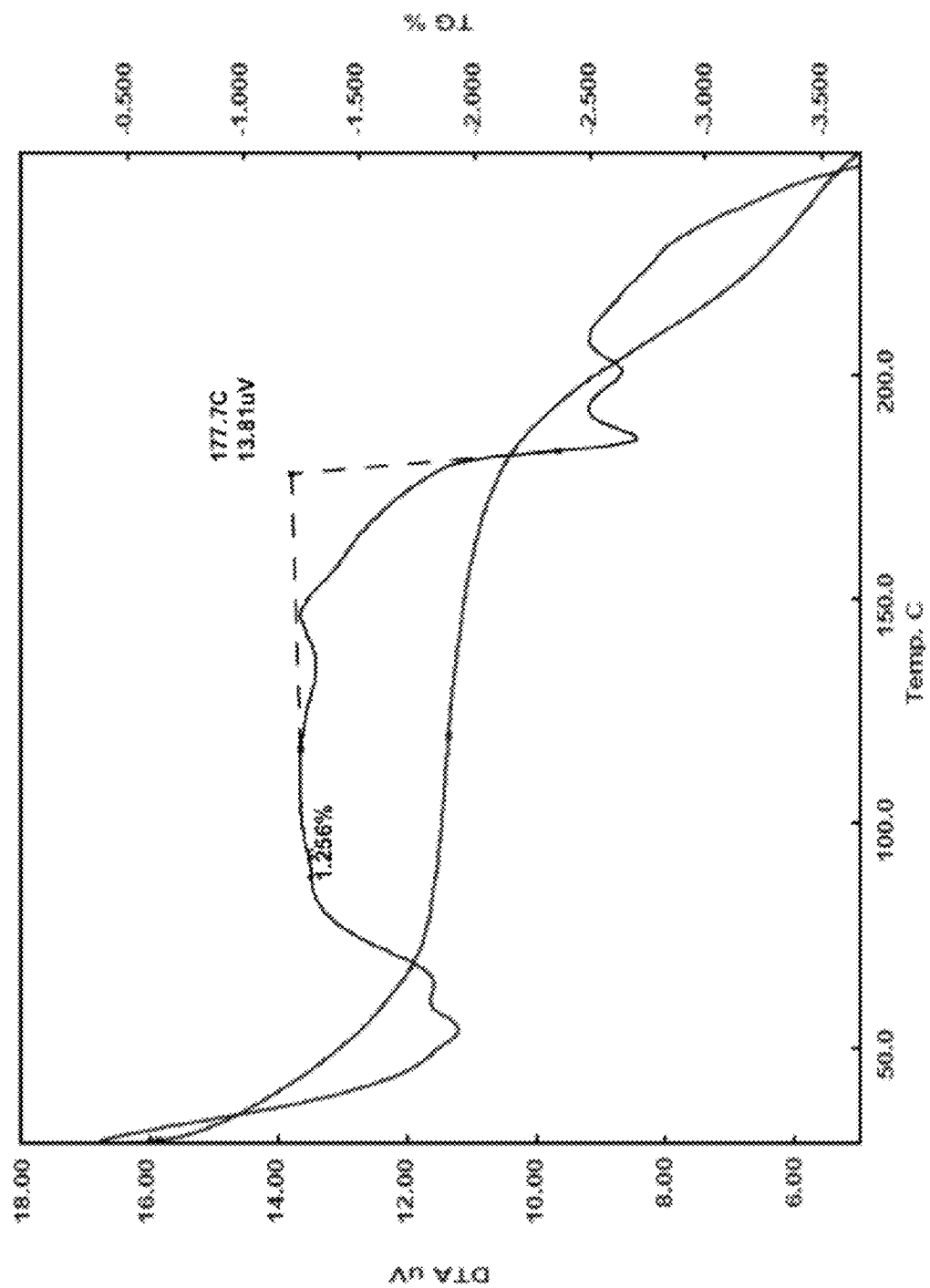
FIG. 3B: TG/DTA results for compound of Formula I as mesylate salt.
Figure 4A:
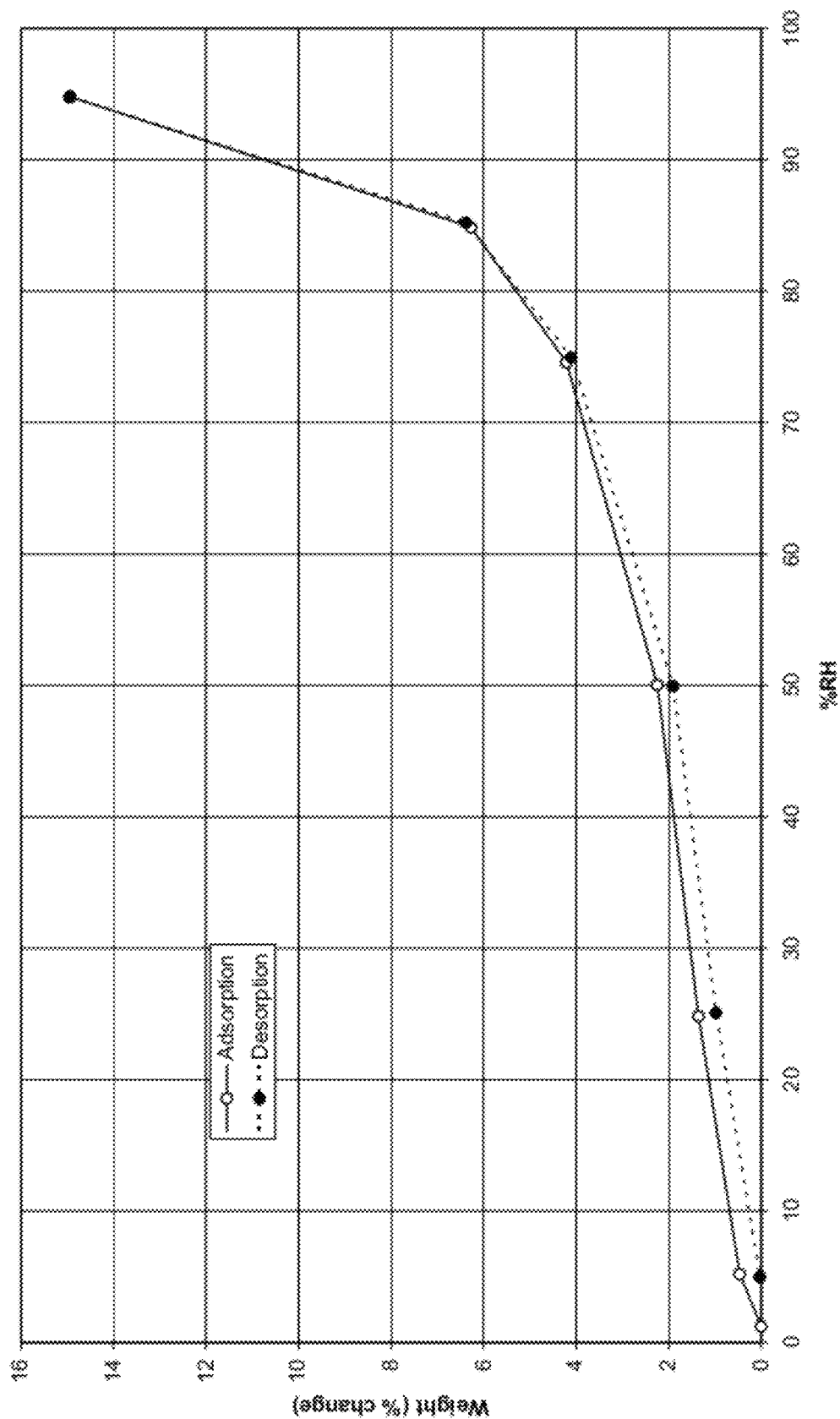
FIG. 4A: Sorption results for compound of Formula I as esylate salt.
Figure 4B:
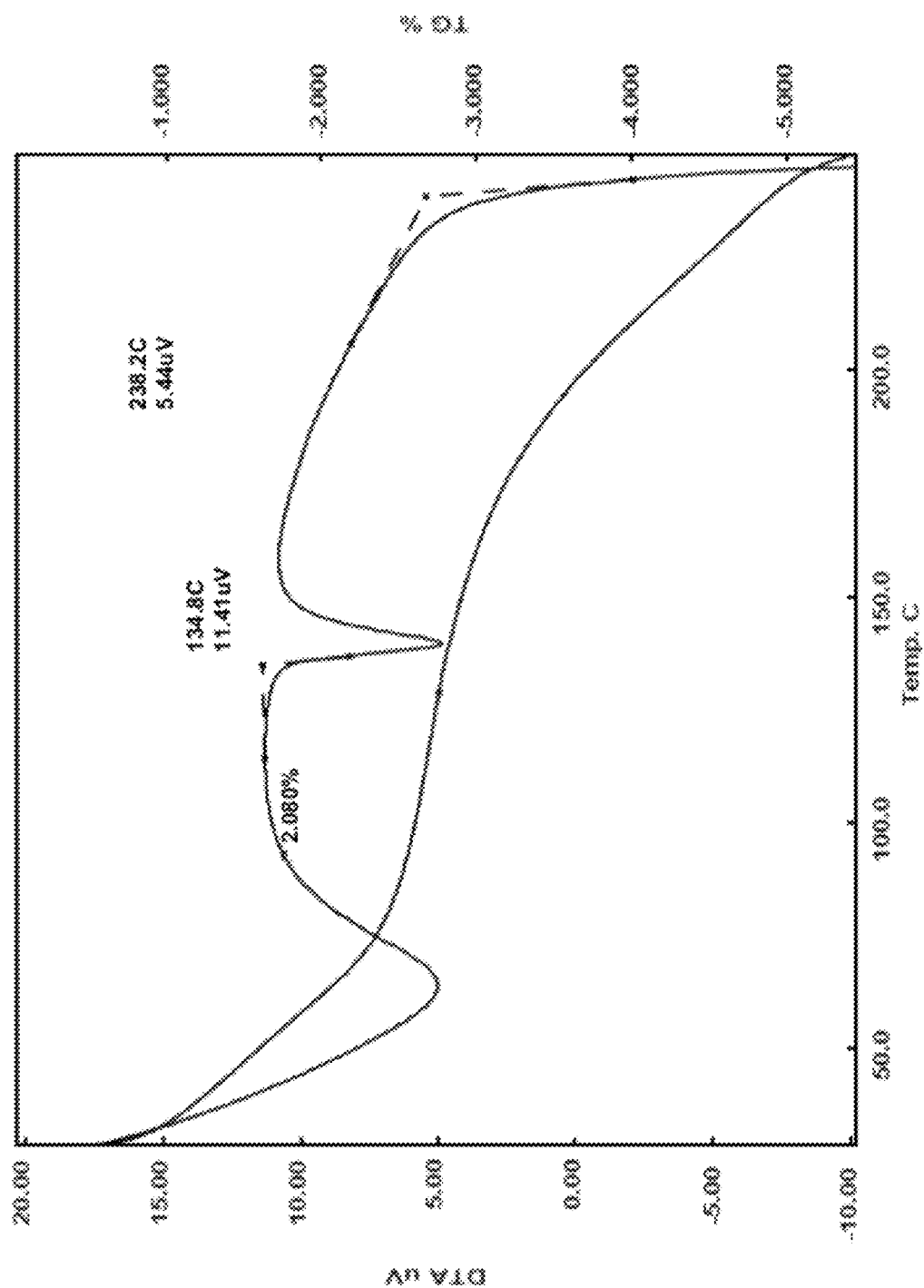
FIG. 4B: TG/DTA results for compound of Formula I as esylate salt.
Figure 5A:
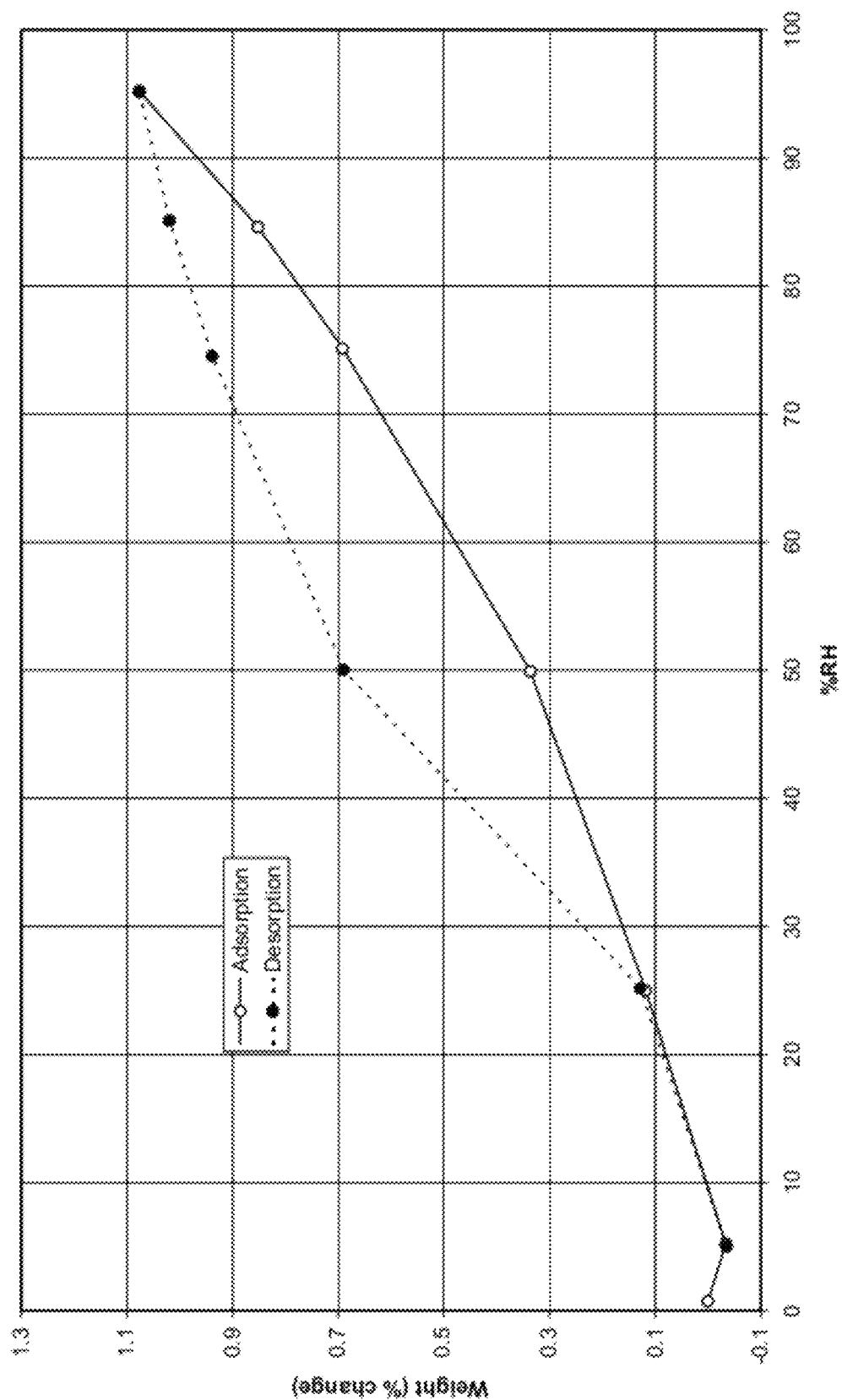
FIG. 5A: Sorption results for compound of Formula I as maleate salt.
Figure 5B:
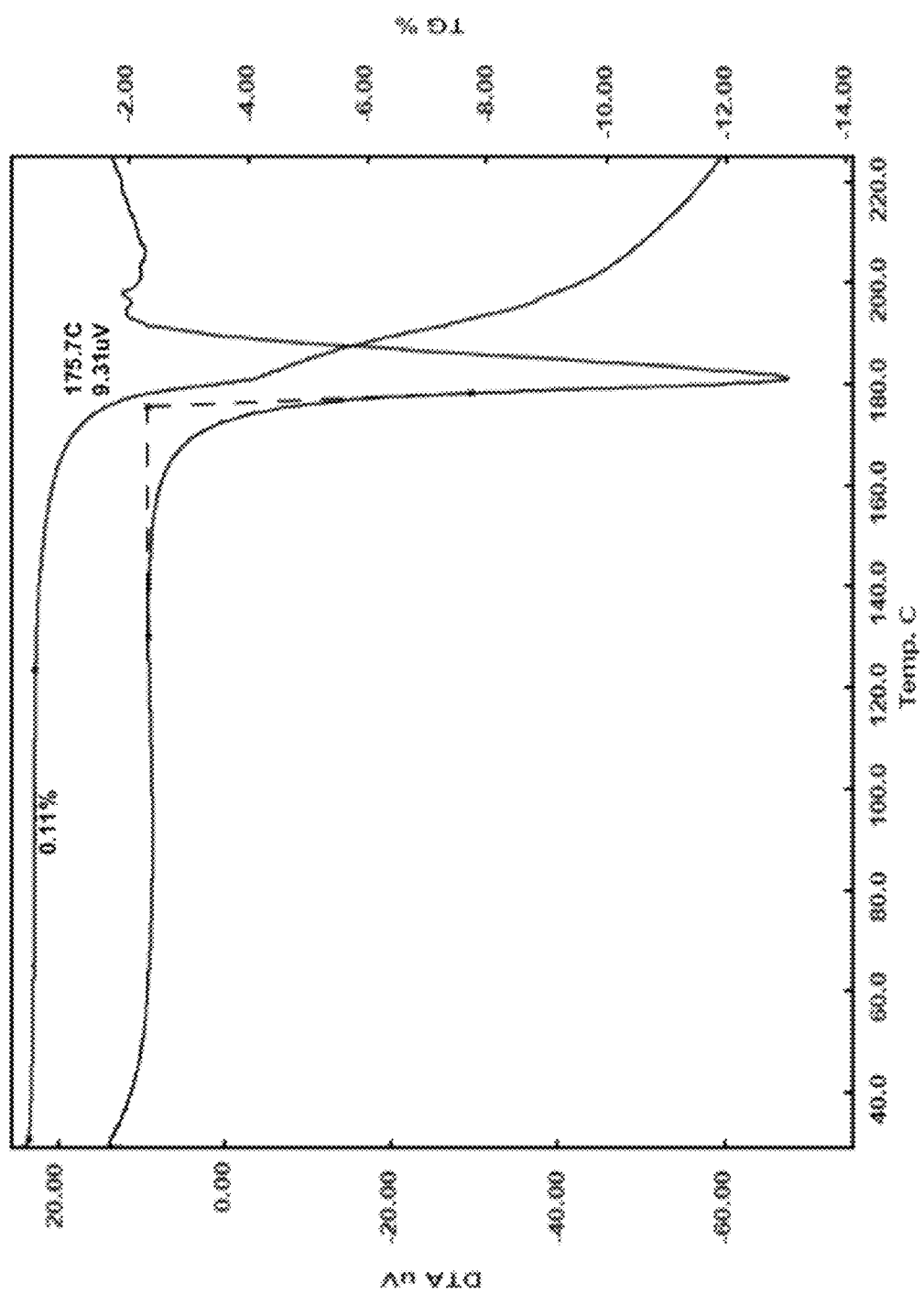
FIG. 5B: TG/DTA results for compound of Formula I as maleate salt.
Figure 6:
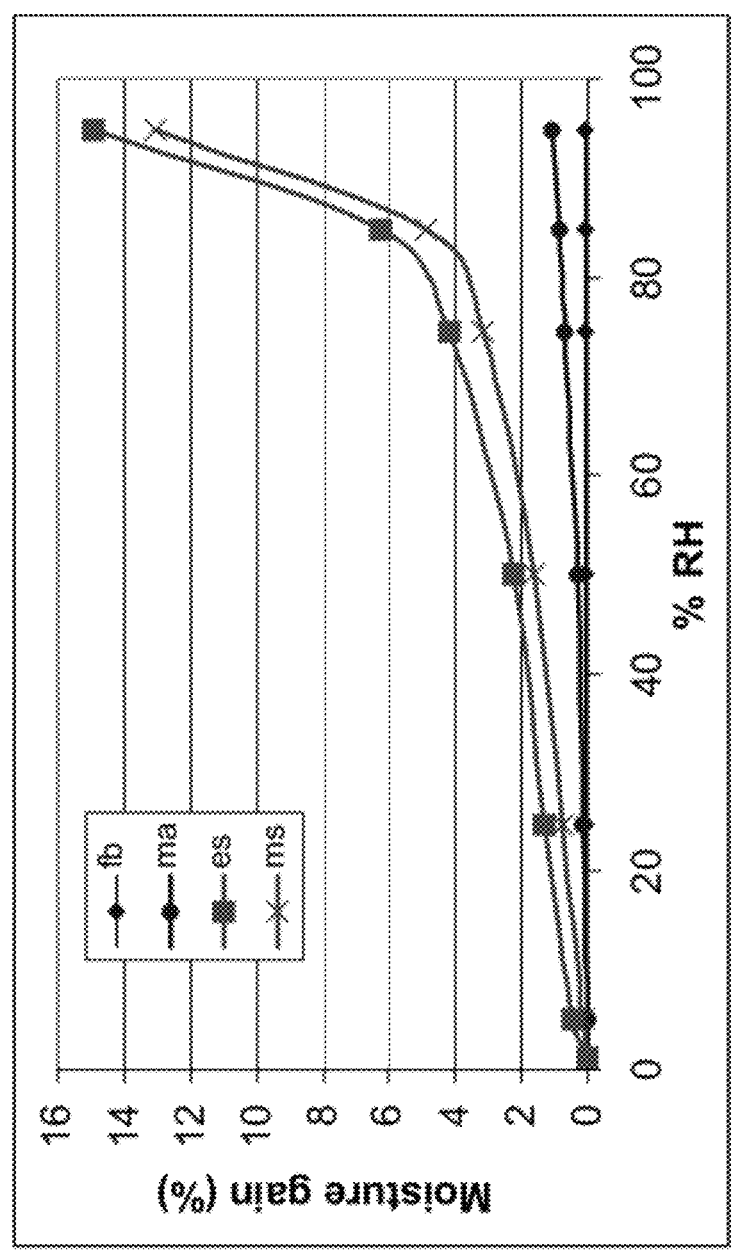
FIG. 6: Overlay graph of sorption results for the free base and salts of the compound of Formula I: -♦-, free base; -●-, maleate salt; -■-, esylate; -x-, mesylate.

Salt Properties and Morphology. Unlike the well formed crystals of the free base, crystals of all three salts tended to be less well formed (See FIG. 1A-D), Thermogravimetric data of the free base and maleate (FIGS. 2A and 5A) shows that the former is a hydrate and the latter is free of residual solvents (LOD 0.1%). The differential thermal analysis (DTA) pattern of the maleate is flat up to its melt, the melt endotherm shows a strong homogeneous transition (FIG. 5B). In contrast, the mesylate and esylate salts have relatively high loss on drying (FIGS. 3A and 4A) suggesting that the samples have residual solvents or volatile impurities. In addition, their DTA patterns show multiple weak transitions indicating phase changes with heating. The moisture sorption profiles show the free base to be non-hygroscopic, the maleate to be slightly hygroscopic, and both the mesylate and esylate to be hygroscopic. An overlay of the sorption profile is shown in FIG. 6.

Example 7

Bioavailability Study of API and Salts of API in Dogs

Bioavailability of the free base, maleate and mesylate salts of the API was studied in beagle dogs. For comparison, a microemulsion of the free base was also studied. The study was performed with 4 dogs, weighing 9-15 kg each. A crossover design with a washout period of at least 1 week was used. The dogs were given a single oral dose of 100 mg of test compound, administered under fasting conditions. Blood samples for determination of the plasma concentrations of API were collected for up to 48 hours after dosing. The plasma samples were analyzed for API concentration by HPLC-mass spectrometry. Data from a previous study in dogs was used to determine the bioavailability of the free base, maleate, and mesylate salts relative to the microemulsion of the free base.

Figure 7:
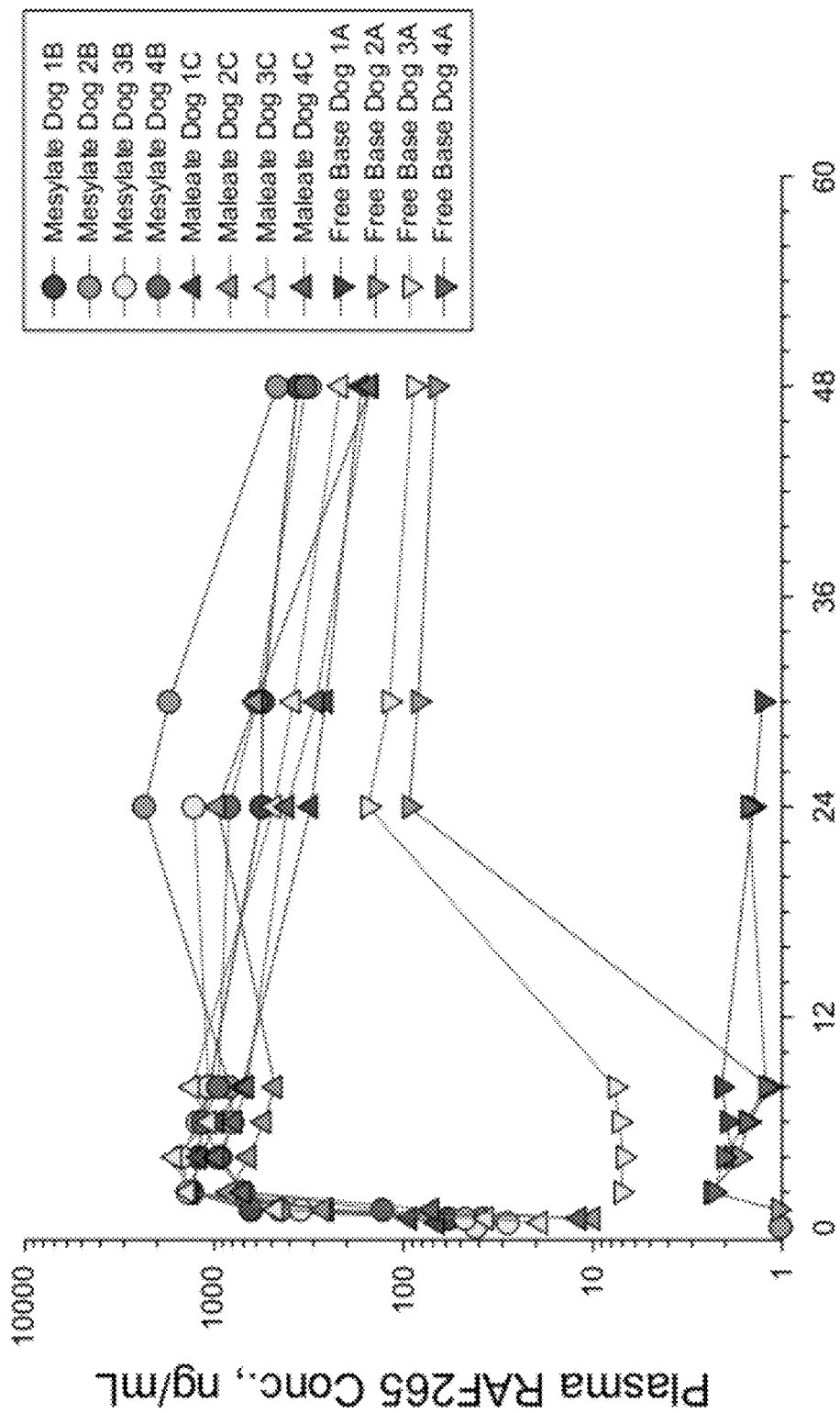
FIG. 7: Plasma concentrations of the free base, mesylate and esylate salts of the compound of Formula I after a single 100 mg oral dose.

Results of the study are shown in FIG. 7. As may be seen in FIG. 7, API as the free base exhibited low and slow oral adsorption. The mesylate and maleate salts had much improved oral adsorption with higher $C_{max}$ than the free base. Table 10 contains a summary of pharmacokinetic parameters measured during the study.

TABLE 10

| Pharmacokinetic Parameters of API After Single 100 mg Oral Dose in Dogs | | | | | | | |
|---|---|---|---|---|---|---|---|
| Formulation | $T_{lag}$ h | $T_{max}$ h | $C_{max}$ ng/mL | $AUC_{0-\infty}$ ng · h/mL | $T_{1/2}$ h | Absolute $F^b$ | Relative $F^c$ |
| Free Base | 1.0 (0.5-2.0) | 16.0 (2.0-24.0) | 62.9 ± 74.4 | 5310 ± 4514 | nd | 2.32 ± 1.97 | 11.4 ± 9.7 |
| Maleate | 0.12 (0-0.25) | 4.0 (2.0-24.0) | 1218 ± 320 | 29646 ± 5916 | 18.8 ± 7.7 | 12.9 ± 2.6 | 63.9 ± 12.7 |
| Mesylate | 0.13 (0-0.5) | 5.0 (2.0-24.0) | 1573 ± 530 | 54364 ± 14184 (n = 3) | 21.4 ± 13.0 (n = 3) | 23.7 ± 6.2 | 117 ± 31 |
| Micro Emulsion (normalized to 10 mg/kg) | | 6 | 3070 | 46416 | 10.8 | 20.3 | |

[a]Median (range) for Tlag and Tmax and mean and sd for other parameters
[b]Relative to an iv dose of 1.25 mg/kg
[c]relative to the micro emulsion

What is claimed is:

1. A composition comprising a pharmaceutically acceptable acid salt of {1-methyl-5-[2-(5-trifluoromethyl-1H-imidazol-2-yl)-pyridin-4-yloxy]-1H-benzoimidazol-2-yl}-(4- trifluoromethyl-phenyl)amine selected from a maleate salt and a methane sulfonate salt and a surfactant.

2. The composition of claim 1 wherein the amount of pharmaceutically acceptable acid salt of {1-methyl-5-[2-(5-trifluoromethyl-1H-imidazol-2-yl)-pyridin-4-yloxy]-1H-benzoimidazol-2-yl}-(4-trifluoromethyl-phenyl)amine is from about 0.0025 wt % to about 80 wt % based upon the total weight of the composition.

3. The composition of claim 1 wherein the surfactant has an HLB value of about 8 or higher than 8.

4. The composition of claim 1 wherein the surfactant is selected from polyoxyethylene castor oil compounds, polyoxyethylene mono- and di-fatty acid esters, mixtures of polyoxyethylene mono- and di-esters of $C_8$-$C_{22}$ fatty acids and glyceryl mono- di-, and triesters of $C_8$-$C_{22}$ fatty acids, α-tocopheryl polyethylene glycol 1000 succinate, polyoxyethylene-polyoxypropylene copolymers, polyoxyethylene sorbitan fatty acid esters, polyoxyethylene alkyl ethers, sodium dioctyl sulfosuccinate, sodium lauryl sulfate, sorbitan fatty, acid esters, sugar fatty acid esters, or a mixture of any two or more thereof.

5. The composition of claim 1 wherein the surfactant is polyoxyl 35 castor oil, polyoxyl 40 hydrogenated castor oil, polyoxyl 60 hydrogenated castor oil, polysorbate 20, polysorbate 40, polysorbate 60, polysorbate 80, polyoxyl 40 stearate, polyoxyl 150 stearate, polyoxyl 150 distearate, d-α-tocopheryl polyethylene glycol 1000 succinate, poloxamer 124, poloxamer 188, poloxamer 407, sorbitan monolauryl ester, sorbitan monopalmityl ester, sorbitan monostearyl ester, or a mixture of any two or more thereof.

6. The composition of claim 1 wherein the surfactant is d-α-tocopheryl polyethylene glycol 1000 succinate, poloxamer 188, or a mixture of any two or more thereof.

7. The composition of claim 1 wherein at least 90 wt % of a sample of the composition containing the equivalent of about 100 mg of {1-methyl-5-[2-(5-trifluoromethyl-1H-imidazol-2-yl)-pyridin-4-yloxy]-1H-benzoimidazol-2-yl}-(4-trifluoromethyl-phenyl)amine dissolves in 900 mL of simulated gastric fluid at 37±0.5° C. in about 90 minutes or less than 90 minutes.

8. The composition of claim 1 wherein the composition is solid.

9. The composition of claim 1 further comprising a carrier.

10. The composition of claim 1 further comprising an antioxidant, a coloring agent, a cyclodextrin, a flavoring agent, a preservative, a sweetener, or a mixture of any two or more thereof.

11. The composition of claim 1 wherein the composition is contained within a capsule or tablet.

12. A method for preparing the composition of claim 1 comprising combining a pharmaceutically acceptable acid salt of {1-methyl-5-[2-(5-trifluoromethyl-1H-imidazol-2-yl)-pyridin-4-yloxy]-1H-benzoimidazol-2-yl}-(4-trifluoromethyl-phenyl)amine and a surfactant to provide the composition of claim 3.

13. A method for preparing the composition of claim 1 comprising combining a compound, {1-methyl-5-[2-(5-trifluoromethyl-1H-imidazol-2-yl)-pyridin-4-yloxy)-1H-benzoimidazol-2-yl}-(4-trifluoromethylphenyl)amine, a pharmaceutically acceptable acid, and a surfactant to provide the composition of claim 3.

14. The method of claim 13 wherein the compound and the acid are mixed by
dissolving the compound and the acid in an organic solvent to form the salt of the compound.

15. The method of claim 14 wherein the organic solvent is a ketone, alcohol, ether, ester or a mixture of any two or more thereof.

16. The method of claim 14 wherein the organic solvent is acetone, methanol, ethanol, isopropanol, or mixtures of any two or more thereof.

17. The method of claim 13 further comprising combining a carrier with the acid salt and the surfactant.

18. The method of claim 13 further comprising combining an antioxidant, a coloring agent, a cyclodextrin, a flavoring agent, a preservative, a sweetener, or a mixture of any two or more thereof with the acid salt and the surfactant.

19. A method of treating cancer and/or inhibiting angiogenesis comprising administering the composition of claim 1 to a subject in need thereof, wherein the cancer to be treated is one or more selected from the group consisting of bladder, breast, brain, head and neck, liver, biliary tract, carcinomas, acute and chronic lymphoid leukemias, acute and chronic myelogenous leukemias, chronic myelomonocytic leukemias colorectal, gastric, gastrointestinal stromal, glioma, lymphomas, melanomas, multiple myeloma, myeloproliferative diseases, neuroendocrine, lung, pancreatic, prostate, renal cell, sarcomas, and thyroid cancers.

20. The composition of claim 1 wherein the salt is the maleate salt.

21. The composition of claim 20 wherein the surfactant has an HLB value of about 8 or higher than 8.

22. The composition of claim 20 wherein the surfactant is selected from polyoxyethylene castor oil compounds, polyoxyethylene mono- and di-fatty acid esters, mixtures of polyoxyethylene mono- and di-esters of $C_8$-$C_{22}$ fatty acids and glyceryl mono-, di-, and triesters of $C_8$-$C_{22}$ fatty acids, α-tocopheryl polyethylene glycol 1000 succinate, polyoxyethylene-polyoxypropylene copolymers, polyoxyethylene sorbitan fatty acid esters, polyoxyethylene alkyl ethers, sodium dioctyl sulfosuccinate, sodium lauryl sulfate, sorbitan fatty acid esters, sugar fatty acid esters, or a mixture of any two or more thereof.

23. The composition of claim 20 wherein the surfactant is polyoxyl 35 castor oil, polyoxyl 40 hydrogenated castor oil, polyoxyl 60 hydrogenated castor oil, polysorbate 20, polysorbate 40, polysorbate 60, polysorbate 80, polyoxyl 40 stearate, polyoxyl 150 stearate, polyoxyl 150 distearate, d-α-tocopheryl polyethylene glycol 1000 succinate, poloxamer 124, poloxamer 188, poloxamer 407, sorbitan monolauryl ester, sorbitan monopalmityl ester, sorbitan monostearyl ester, or a mixture of any two or more thereof.

24. The composition of claim 20 wherein the surfactant is d-α-tocopheryl polyethylene glycol 1000 succinate, poloxamer 188, or a mixture of any two or more thereof.

* * * * *